United States Patent
Blake et al.

(10) Patent No.: US 7,819,796 B2
(45) Date of Patent: Oct. 26, 2010

(54) EMBRYO MODIFICATION AND IMPLANTATION

(75) Inventors: Deborah A. Blake, Auckland (NZ); Nicola L. Carter, Auckland (NZ); Stephen M. Henry, Howick (NZ)

(73) Assignee: Kode Biotech Limited, Auckland (NZ)

( * ) Notice: Subject to any disclaimer, the term of this patent is extended or adjusted under 35 U.S.C. 154(b) by 1326 days.

(21) Appl. No.: 10/510,377

(22) PCT Filed: Apr. 7, 2003

(86) PCT No.: PCT/NZ03/00059

§ 371 (c)(1),
(2), (4) Date: Nov. 7, 2005

(87) PCT Pub. No.: WO03/087346

PCT Pub. Date: Oct. 23, 2003

(65) Prior Publication Data

US 2006/0089523 A1   Apr. 27, 2006

(30) Foreign Application Priority Data

Apr. 5, 2002   (NZ) ...................... 518163

(51) Int. Cl.
*A61B 17/435* (2006.01)
(52) U.S. Cl. ...................................... 600/34
(58) Field of Classification Search ............. 600/33–35; 128/897, 898
See application file for complete search history.

(56) References Cited

U.S. PATENT DOCUMENTS

| | | | |
|---|---|---|---|
| 6,177,059 B1 | 1/2001 | Matsuda et al. | |
| 6,196,965 B1 | 3/2001 | Purdum | |
| 6,210,707 B1 | 4/2001 | Papahadjopoulos et al. | |
| 6,309,843 B1 * | 10/2001 | Timms | 435/7.1 |
| 6,352,831 B1 | 3/2002 | Buschard et al. | |

FOREIGN PATENT DOCUMENTS

| | | | | |
|---|---|---|---|---|
| WO | WO 99/05255 | * | 2/1999 | 600/34 |

OTHER PUBLICATIONS

Taylor et al., "Complement-binding proteins are strongly expressed by human preimplantaion blastocysts and cumulus cells as well as gametes", Molecular Human Reproduction, 2(1), 52-59, 1996.

Zhu et al., "Glycosphingolipids of rabbit endometrium and their changes during pregnancy", J. Reprod. Fert. 95, 813-823.

Taylor, C.T., et al; "Complement-binding proteins are strongly expressed by human preimplantation blastocysts and cumulus cells as well as gametes"; *Molecular Human Reproduction*, vol. 2, No. 1, pp. 52-59 (1996).

(Continued)

*Primary Examiner*—Samuel G Gilbert
(74) *Attorney, Agent, or Firm*—Nixon & Vanderhye

(57) ABSTRACT

The present invention relates to constructs and methods used to enhance the attachment and implantation of an embryo. It is shown that modified glycolipids and glycolipid-attachment molecule constructs can be used to modify embryos, or localised to target tissues, to enhance interaction between the embryo and the target tissue, (typically the endometrium). The invention may advantageously be used to enhance implantation of embryos in the uterus, for example, in IVF treatments.

32 Claims, 6 Drawing Sheets

OTHER PUBLICATIONS

Figure 1:
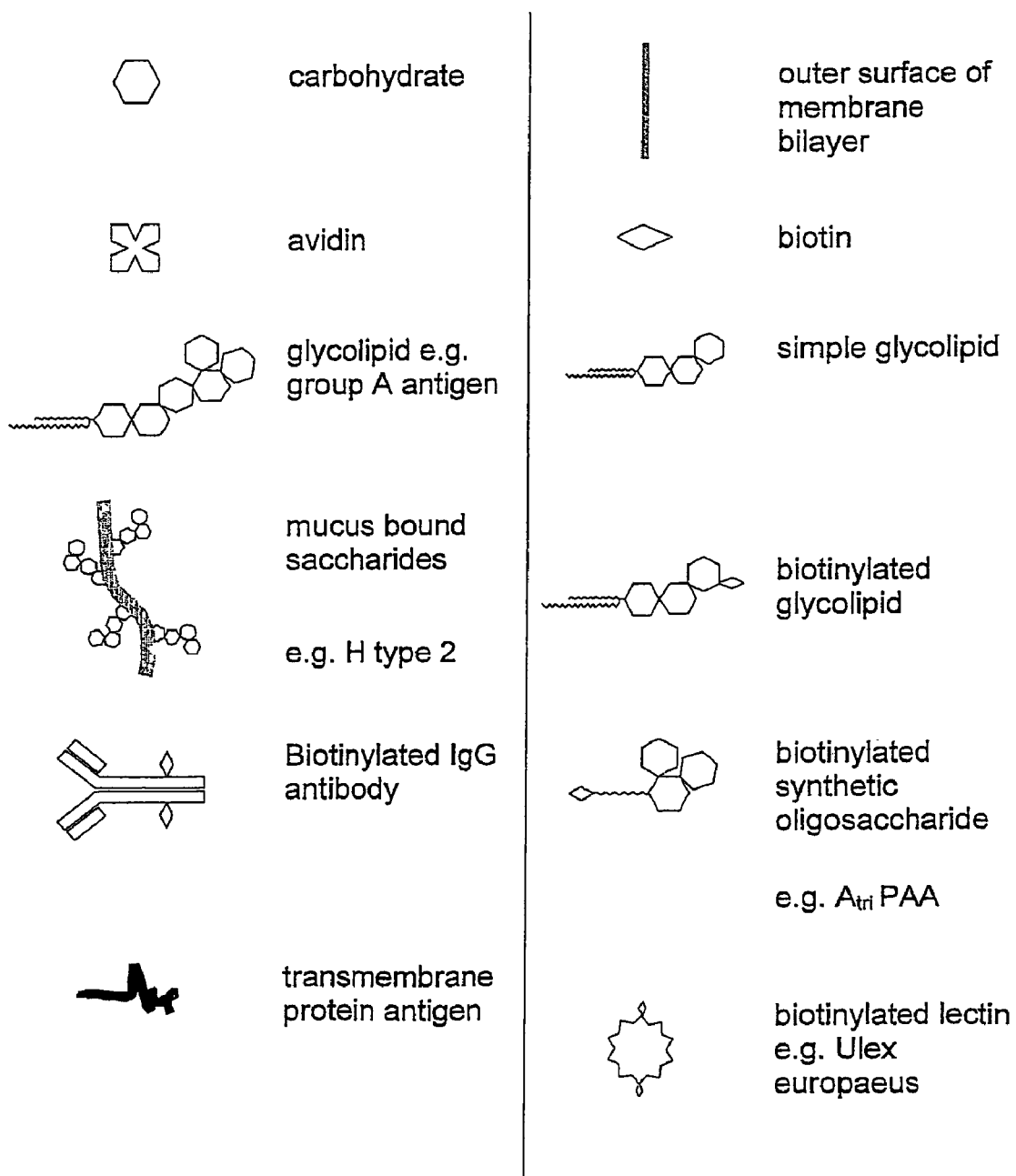

Zhu, Z., et al; "Clycosphingolipids of rabbit endometrium and their changes during pregnancy"; *Journals of Reproduction & Fertility Ltd.*, vol. 95; pp. 813-823 (1992).

Simon, C., et al; "Early pregnancy losses in in vitro fertilization and oocyte donation"; *Fertility and Sterility*, vol. 72, No. 6, pp. 1061-1065 (1999).

* cited by examiner

EMBRYO MODIFICATION AND IMPLANTATION

This invention relates to constructs and methods used to enhance the implantation of an embryo into the uterus. In particular, the invention relates to modified embryos which have been modified by the insertion into the cell membrane (or zona pellucida) of the embryo of constructs which have a binding affinity for mucus or cell membrane surfaces, or enhance cellular interactions.

BACKGROUND

Each year 15% of couples seek medical advice because of difficulties becoming pregnant (WHO 1997). Sub-fertility is therefore currently one of the most frequent health concerns facing the population aged 25-45 years. For the past two decades, in vitro fertilisation (IVF) has provided an effective form of assistance for a large proportion of these couples. Indeed, IVF now accounts for 1.3% of all live births in Europe (Nygren et al. 2001) and 1.7% of all live births in Australasia (Hurst et al. 2001).

From the inception of routine IVF in 1978, pregnancy rates have risen steadily to levels considered normal for the fertile population (approximately 25% per attempt). The quest to break through this physiological barrier is driven by the significant financial and emotional cost for each IVF treatment for individuals.

Failure of embryos to implant into the lining of the uterus (endometrium) during an IVF treatment cycle is widely accepted by health professionals as the most significant limiting factor to improving success rates. The scale of embryo wastage following transfer into IVF patients is enormous, such that 80-85% of embryos fail to result in a pregnancy (Blake et al 2002). Recent analysis of daily urine levels of human chronic gonadotrophin (hCG) in women undergoing an IVF cycle, demonstrated that implantation was detected in as many as 60% of the cycles (Simon et a/1999). Of all embryos transferred in an IVF, 40% fail to implant.

There are two broad reasons for failure of implantation following replacement of apparently viable embryos. The first involves intrinsic embryonic factors that reflect retarded development or deficiencies in the health of the blastocyst itself and its ability to hatch (Gott et al 1990, Plachot 1992, van Kooij et al 1996). The second relates to extrinsic factors that imply a lack of implantation receptivity in the endometrium (Edwards 1986, Yaron 1994). Moreover, successful implantation is dependent on the synchrony of embryonic development and endometrial maturation that is largely controlled by the ovarian hormone milieu.

Recently it has become apparent that fertility drugs used for the super-ovulation of women undergoing IVF are predominantly responsible for the compromised implantation receptivity observed on both sides of the embryonic/maternal interface. Ertzeid and Storeng demonstrated the detrimental effects of gonadotropins on implantation using a series of cross-over embryo transfer experiments (Ertzeid et al. 2001). Embryos from super-ovulated and non-stimulated females were transferred to separate uterine horns in the same super-ovulated or non-stimulated pseudo-pregnant recipient mice. A significant decrease in implantation was observed in the uterine horns receiving embryos from super-ovulated donors and even more dramatically in both horns of super-ovulated recipients.

Highly elevated concentrations of estrogen result from ovarian stimulation in IVF. These are suspected to alter the cascade of hormonal events and subsequent expression of cytokines that the oocytes, embryos and uterine endometrium would ordinarily be exposed to in an unstimulated menstrual cycle. Add to this the physiological challenge of in vitro culture, largely devoid of growth factors, and it is not unexpected that IVF derived embryos might be compromised at the time of implantation.

Despite substantial advances in the recovery and maturation of multiple occytes from unstimulated cycles, the practice of oocyte in vitro maturation (IVM) is as yet clinically unaccepted. With the prospect that super-ovulation will remain the mainstay of IVF, other approaches to improving implantation rates continue to be explored.

The development of physiological based culture media constituents has gone some way to improving the development of embryos in culture for up to 6 days. This extended culture enables self-selection of the most viable embryos for transfer, but as a consequence this approach has a high attrition rate of embryos. Co-culture of embryos on a mono- or bi-layer of support cells (e.g. endometrial cells) has also provided a method for improving the development of embryos in culture presumably via the stimulus of growth factors. More directly the addition of a variety of growth factors to media has been explored and shown to be of benefit (Sjoblom et al. 2000).

Maintaining a receptive endometrium through administration of human chorionic gonadotropin or progesterone has been practiced since the early days of IVF. In fact only after additional progesterone support was given in the luteal phase of the cycle, did the world's first IVF pregnancies result. It has long been recognised that the elevated estrogen profiles produced by the fertility drugs effectively advance the endometrial tissue dating by approximately one day (Noyes et al., 1950; Pittaway et al. 1983; Garcia et al. 1984). Compound this with the fact that embryos are routinely transferred into the uterus at the 2-8 cell stage (48-72 hrs prematurely to what occurs naturally) and it is clear that IVF results in an asynchronous environment for implantation.

Implantation of a hatched blastocyst is described as consisting of three phases:
a) apposition— where the embryo comes into initial physical contact with the glycoconjugate coat of the endometrial epithelium (called the glycocalyx).
b) adhesion— where the embryo undergoes cell to cell, and cell to matrix binding with molecules derived from the apical cells on the endometrium.
c) invasion— where the embryo penetrates through the epithelial layer of the endometrium by intruding between cell junctions as occurs in the human or by displacement of the cells found in some animals (e.g. mice).

Super-ovulation has been postulated to alter electronegative properties of the glycocalyx and apical cell surface of the endometrium. In this way; fertility drugs may reduce effective apposition and adhesion of a transferred embryo (Ronnberg et al. 1985).

At least two therapeutic approaches to improving implantation rates in IVF embryos have been practiced in humans. The first draws on the observation that inclusion of the glycoaminoglycan, hyaluronan, in the media containing embryos for transfer, results in a higher implantation rate than media devoid of this polysaccharide (Gardner et al. 1999). The concentration of hyaluronan increases in the uterus at the time of implantation in the mouse (Zorn et al. 1995) and is suggested to facilitate implantation by a variety of means such as increasing cell-cell and cell-matrix adhesion and indirectly through promotion of angiogenesis. Despite a lack of published trials in humans, hyaluronate is now present in a number of commercially available embryo transfer media.

One therapy that has undergone clinical trials and is described in U.S. Pat. No. 6,196,965, is the use of a fibrin sealant. The first experiments with a fibrin sealant were carried out in 1981, and by 1988 it had been proven safe to use in humans (Rodrigues et al. 1988).

U.S. Pat. No. 6,196,965 is based on the technique used in a randomised clinical trial published in 1992 (Feichtinger et al. 1992). Embryos are transferred in a catheter, sandwiched between small quantities of thrombin/aprotinin and then fibrin. The results of the trial demonstrated no significant difference in pregnancy rate between the control and treatment group (546 patients), but a significant decrease in ectopic pregnancies in the fibrin sealant group.

The rationale and theoretical basis for the two therapeutic approaches described above are different. Hyaluronate is added to transfer media in the hope that it will induce a more physiologically receptive environment for implantation. There is, however, an absence of direct evidence at the molecular level proving this hypothesis. Fibrin sealant therapy on the other hand, is used to encase the embryos in an adhesive plug that will theoretically be glued onto the endometrium. Expulsion of embryos from the uterine cavity by muscular contraction and avoidance of ectopic pregnancy was the predominant motivation for the fibrin sealant in the Feichtinger trial (Feichtinger et al. 1990), although other investigators have hypothesised that fibrin would improve the adhesion phase of implanting embryos (Rodrigues et al. 1988).

In addition to the previously described therapeutic approaches, the specification for international application no. PCT/US98/15124 (published as WO 99/05255) describes the enhancement of implantation by contacting the embryo with a lipid-modified adhesion molecule so as to modify the development of the embryo. The technique of "protein painting" embryos with glycosylphosphatidylinositol (GPI) linked Qa-2 proteins to increase the cell division rate is described.

Protein painting is a method for modifying the external antigens of cell membranes without gene transfer. The method exploits the ability of GPI linked proteins to spontaneously anchor to cell membrane via their lipid tails. The method described in the specification for international application no. PCT/US98/15124 (WO 99/05255) requires that a naturally occurring (or genetically altered) protein is inserted into an embryo membrane with an attached GPI lipid tail. Isolated GPI-anchored proteins are stated as having an unusual capacity to reintegrate with a cell-surface membrane. The molecules that can be used for modifying an embryo in this way are therefore confined to a rather limited group.

As described herein, the inventors have now found that embryos can be modified with a range of selected synthesised molecules (modified glycolipids and glycolipid-attachment molecule constructs) and have the ability to bind with mucus, and/or mucus components, and/or cell membranes. The molecules are prepared exogenously by chemical or biological processes.

Not only has the modification of embryos by the method of the invention been successfully demonstrated in an in vitro culture system, but animals have given birth to healthy offspring derived from modified embryos. Embryos prepared in accordance with the invention appear to be developmentally indistinguishable from their unmodified counterparts.

It is an object of this invention to provide a modified embryo for the enhanced implantation of the embryo into the endometrium of an animal, or to at least provide the public with a useful choice.

STATEMENTS OF INVENTION

In a first aspect of the invention there is provided a glycolipid-inserted embryo for the preparation of an embryo modified for enhancing the implantation of the embryo into the endometrium of an animal, where:
  the glycolipid-inserted-embryo has an exogenously modified glycolipid having lipid tails inserted into a cell membrane of the embryo or into the zona pellucida of the embryo; and
  the glycolipid has been modified to incorporate a binding part wherein said binding part is adapted to enable binding to an attachment molecule.

Preferably, the glycolipid has been modified to incorporate the binding part prior to the insertion of its lipid tails into the cell membranes of the embryo or into the zona pellucida of the embryo.

In a second aspect of the invention there is provided an embryo modified for enhancing the implantation of the embryo into the endometrium of an animal, where:
  the embryo has an attachment molecule which is capable of attaching to the endometrium; and
  the attachment molecule is linked to the embryo by an exogenously modified glycolipid having lipid tails inserted into a cell membrane of the embryo or into the zona pellucida of the embryo; and
  the attachment molecule and the glycolipid have each been modified to incorporate a binding part adapted to enable the attachment molecule and the glycolipid to be bound together via their respective binding parts either directly or through a bridging molecule.

Preferably, the modification to the glycolipid is to the carbohydrate portion of the glycolipid.

Preferably the attachment molecule is a molecule known or adapted to interact with the endometrium, mucus, mucin, or other endogenous or exogenously provided components of mucus. More preferably the attachment molecule is a known endometrial attachment molecule.

In one embodiment of the invention the binding interaction between the attachment molecule and the glycolipid are bound by way of non-covalent binding interactions including ionic, van de Waals, water exclusion, electrostatic, hydrogen bonding and chelation binding or via covalent bonding.

In one embodiment of the invention the binding interaction between the attachment molecule and the glycolipid is avidin-biotin binding. In one preferred embodiment the binding part of the glycolipid comprises biotin and the binding part of the attachment molecule comprises avidin. In an alternative preferred embodiment the binding part of the glycolipid comprises avidin and the binding part of the attachment molecule comprises biotin.

In one embodiment of the invention the binding interaction between the attachment molecule and the glycolipid is through a bridging molecule. The bridging molecule may comprise avidin in the case of the binding part of both the attachment molecule and the glycolipid comprising biotin. Alternatively, in the case of the binding part of both the attachment molecule and the glycolipid comprising avidin, the bridging-molecule may comprise biotin.

In one embodiment of the invention the binding interaction between the attachment molecule and the glycolipid may be a chelation interaction. The binding parts of the attachment molecule and the glycolipid may therefore be bridged by a chelated metal ion (e.g. $Co^{2+}$, $Ni^{2+}$ or $Cu^{2+}$) and a polyhistidine recombinant protein. The chelator may be attached covalently or non-covalently (e.g. via biotin or avidin) to the glycolipid.

The glycolipid may be any glycolipid capable of inserting its lipid tails into the cell membranes of the embryo or into the zone pellucida of the embryo such as phosphoglycerides or sphingolipids. The glycolipid may be a natural molecule or a modified (e.g. biotinylated) glycolipid. Preferably the modified glycolipid is a biotinylated glycolipid either of the ganglioside class that contains sialic acid groups, or the neutral class that contains galactose.

The attachment molecule may be any molecule that has a binding affinity for molecules on cell membranes (e.g. receptor sites and blood group related antigens) including their mucus coat. Preferably the cell membrane is endometrial. In particular, the attachment molecule is preferably a protein, a peptide (such as poly L-lysine) a carbohydrate, an acyl group, a polymer, or an immunoglobulin such as immunoglobulin G (IgG) or a lectin. Alternatively, the attachment molecule may be a synthetic molecule (e.g. polyvinyl pyrrolidine, or an acyl group) which reacts with molecules expressed on cell membranes or on the mucus layer covering the cell membrane. The attachment molecule can itself be a glycolipid or glycolipid conjugate.

In a third aspect of the invention there is provided a method of preparing the glycolipid-inserted-embryo of the first aspect of the invention including the step:
contacting a glycolipid with an embryo, where the glycolipid has been exogenously modified to incorporate a binding part, wherein said binding part is adapted to enable binding to an attachment molecule either directly or through a bridging molecule, so that the lipid tails of the glycolipid insert into a cell membrane of the embryo or into the zona pellucida of the embryo.

In a fourth aspect of the invention there is provided a method of preparing the modified embryo of the second aspect of the invention including the steps;
contacting an attachment molecule with a glycolipid, where the attachment molecule and the glycolipid have each been modified to incorporate a binding part adapted to enable the attachment molecule and the glycolipid to bind together via their respective binding parts either directly or through a bridging molecule to provide a glycolipid-attachment molecule construct; and then
contacting the attachment molecule bound to the glycolipid (glycolipid-attachment molecule construct) with an embryo so that the lipid tails of the glycolipid insert into the cell membranes of the embryo or into the zona pellucida of the embryo:
Or including the steps:
contacting a glycolipid with an embryo, where the glycolipid has been exogenously modified to incorporate a binding part adapted to enable binding to an attachment molecule either directly or through a bridging molecule, so that the lipid tails of the glycolipid insert into a cell membrane of the embryo or into the zona pellucida of the embryo; and then
contacting the glycolipid-inserted-embryo with an attachment molecule, modified to incorporate a binding part wherein said binding part is adapted to enable binding to the binding part of the glycolipid either directly or through a bridging molecule.

Preferably the glycolipid, has been modified to incorporate a binding part comprising biotin and the attachment molecule has been modified to incorporate a binding part comprising avidin.

Alternatively, the glycolipid has been modified to incorporate a binding part comprising avidin and the attachment molecule has been modified to incorporate a binding part comprising biotin.

In the case of binding of the glycolipid to the attachment molecule through a bridging molecule, It is preferred that the bridging molecule comprises avidin and that both the glycolipid and the attachment molecule have been modified to incorporate binding parts comprising biotin.

In a fifth aspect of the invention there is provided a method of enhancing the implantation of an embryo into the endometrium of an animal, preferably a human, or domesticated animal, comprising the steps:
preparing a modified embryo according to the second aspect of this invention, and
transferring the modified embryo to the uterus of the animal.

In one embodiment of the invention the modified embryo is prepared from a species, hybrid or variety of animal that is the same as the species, hybrid or variety of animal, to the uterus of which it is transferred. In an alternative embodiment, the species, hybrid or variety differ.

In a sixth aspect of the invention there is provided a glycolipid-attachment molecule construct when used for generating a modified embryo comprising a glycolipid modified to incorporate a binding part and an attachment molecule modified to incorporate a binding part wherein the respective binding parts are adapted to enable the modified glycolipid and the modified attachment molecule to bind each other either directly or indirectly through a bridging molecule.

In a seventh aspect of the invention there is provided a method of enhancing the implantation of an embryo into the endometrium of an animal including the steps of:
introducing a construct of the sixth aspect of the invention into the uterus of the animal so that the construct becomes localised to the endometrium; and then
transferring the embryo to the uterus of the animal.

In an eighth aspect the invention provides a kit for use in enhancing the implantation of an embryo of an animal comprising one or more preparations of a glycolipid-attachment molecule construct of the sixth aspect of the invention.

While the invention is broadly defined as above, those persons skilled in the art will appreciate that it is not limited thereto and that it also includes embodiments of which the following description provides examples. In addition, the present invention will be better understood from reference to the figures of the accompanying drawings.

FIGURES

FIG. 1— Schematic legend

Figure 2:
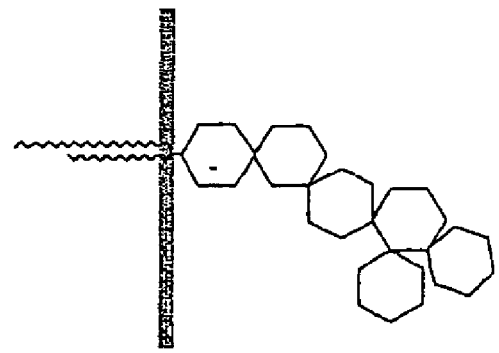

FIG. 2— Schematic representation of natural glycolipid insertion. A naturally occurring glycolipid (e.g. glycolipid A or $Le^b$) is inserted into a cell membrane (e.g. RBC, embryonic cell or endometrial cell).

Figure 3:
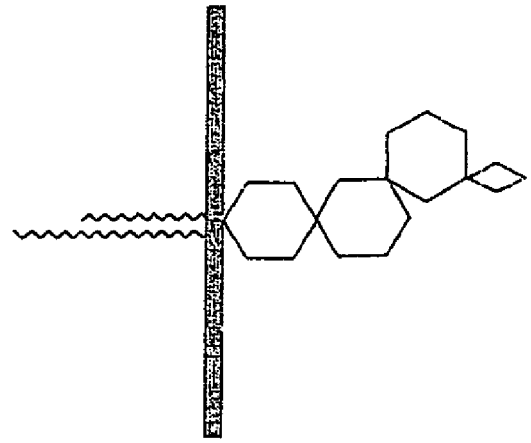

FIG. 3— Schematic representation of biotinylated glycolipid insertion. A biotinylated glycolipid (BioG) is inserted into a cell membrane (e.g. RBC, embryonic, endometrial cell).

Figure 4A:
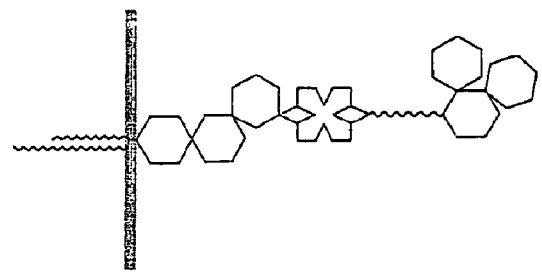

FIG. 4a— Schematic representation of terminal an attachment molecule (synthetic carbohydrate) and a glycolipid bound together. A biotinylated glycolipid (e.g. BioG) is inserted into a cell membrane, conjugated to an avidin molecule and a biotinylated synthesised blood group A antigen (e.g. Atri-PAA) is attached.

Figure 4B:
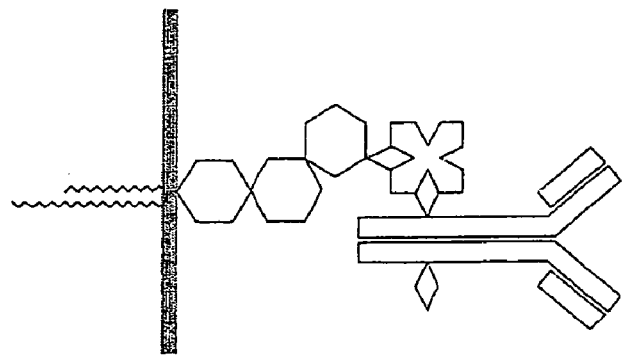

FIG. 4b— Schematic representation of an attachment molecule (IgG) and a glycolipid bound together. A biotinylated glycolipid (e.g. BioG) is inserted into a cell membrane, conjugated to an avidin molecule and a biotinylated IgG is attached.

Figure 4C:
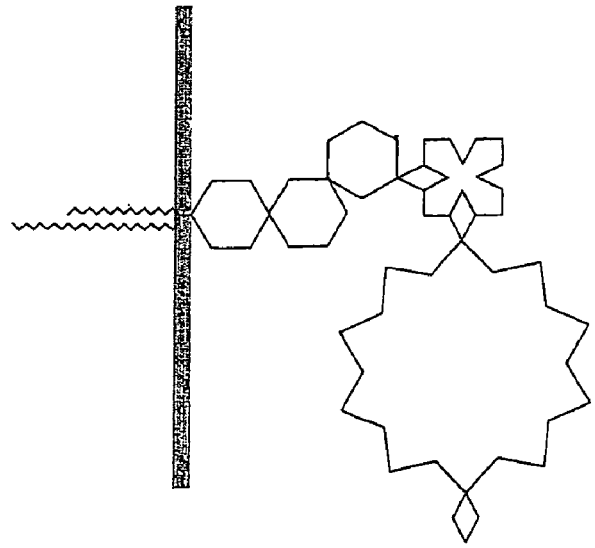

FIG. 4c— Schematic representation of an attachment molecule (lectin) and a glycolipid bound together. A biotinylated glycolipid (e.g. BioG) is inserted into a cell membrane, conjugated to an avidin molecule and a biotinylated lectin is attached.

Figure 5:
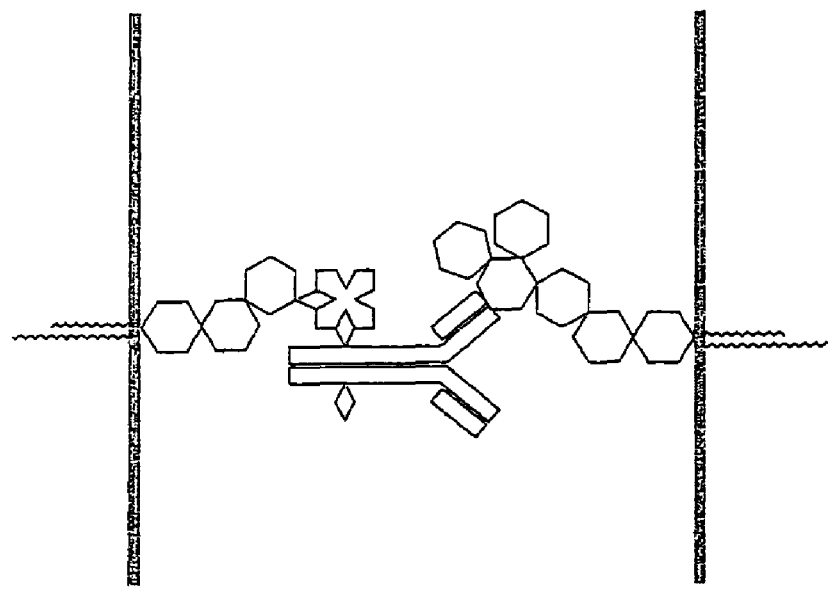

FIG. 5— Schematic representation of the interaction between a modified embryo and a cell type. A BioG transformed cell of an embryo is conjugated to avidin and a biotinylated specific antibody (e.g. BiolgG$^{A,B}$). The resulting antibody transformed cell is then exposed to another cell type (RBC, embryo) expressing the corresponding antigen (e.g. blood group A or B) resulting in adhesion between the two cell types.

Figure 6:
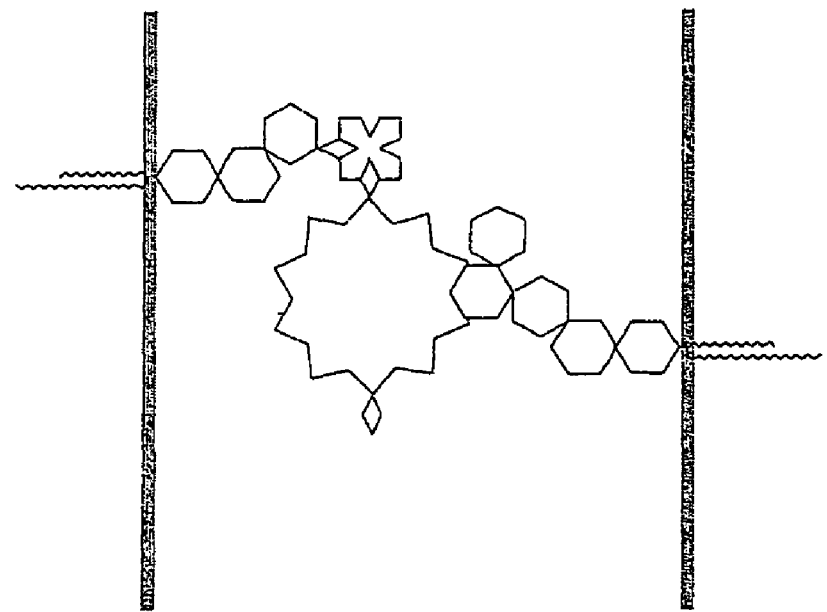

FIG. 6— Schematic representation of the interaction between a modified embryo and a cell type. A BioG transformed cell of an embryo is conjugated to avidin and a biotinylated lectin (e.g. Bio-UE) is attached. The resulting lectin transformed cell is then exposed to another cell type (e.g. endometrial) expressing the corresponding antigen resulting in adhesion between the two cell types.

Figure 7:
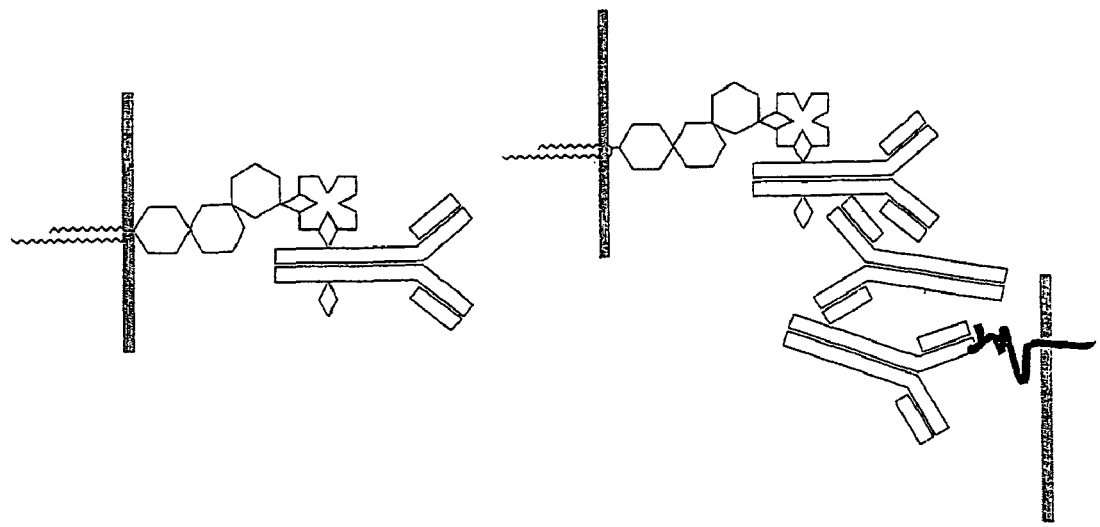

FIG. 7— Schematic representation of BioG/Av/BiolgG insertion into embryos. Adhesion is determined by reaction with antibody sensitised cells (IgG bearing) via anti-human Ig.

Figure 8A:
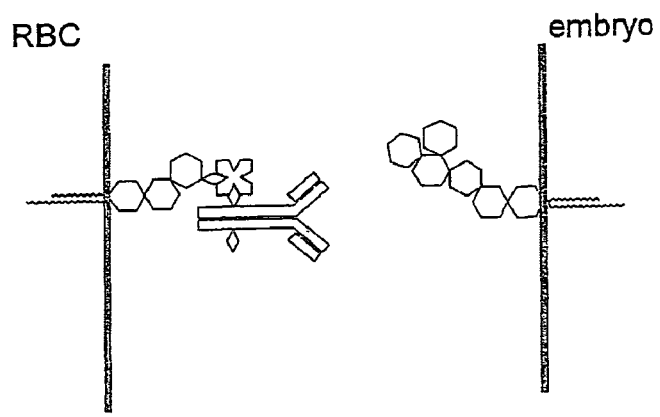

FIG. 8a— Schematic representation of one mechanism for demonstrating the adhesive protein model using BiolgG$^{A,B}$ or BioG/Av transformed mRBCs (murine red cells), and mouse embryos. Mouse embryos (right) will attach to the BiolgG$^{A,B}$ transformed cells (eg RBCs) (left).

Figure 8B:
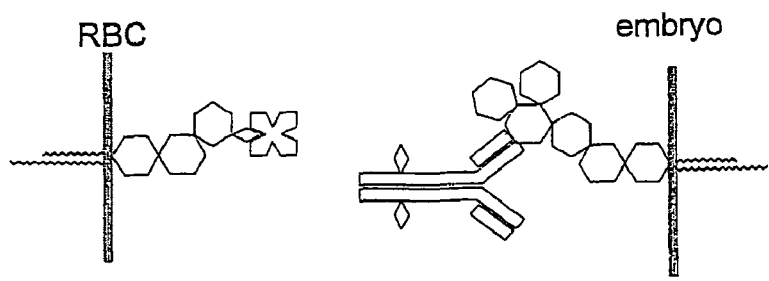

FIG. 8b— Schematic representation of one mechanism for demonstrating the adhesive protein model using BiolgG$^{A,B}$ or BioG/Av transformed mRBCs, and mouse embryos. Mouse embryos (right) that have been exposed to BiolgG$^{A,B}$ (sensitised) will attach to the Bio/Av transformed cells (left).

Figure 9A:
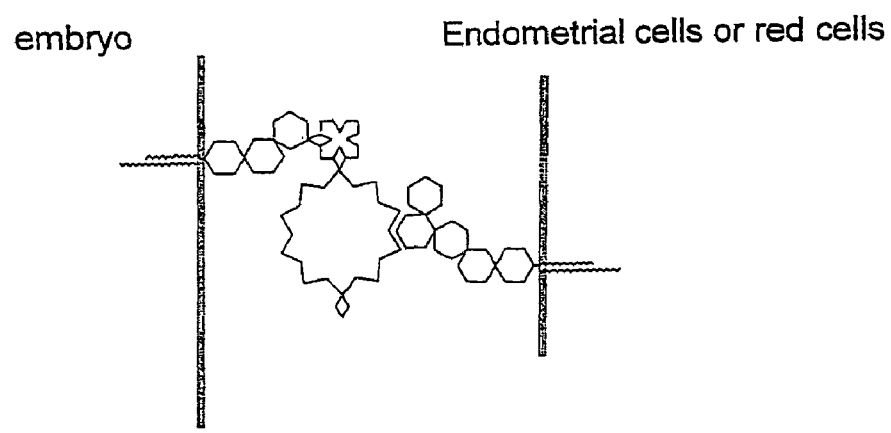

FIG. 9a— Schematic representation of BioUE adhesion model showing direct interaction between a BioUE transformed embryo (left) and H antigen bearing endometrial cells or red cells (right)

Figure 9B:
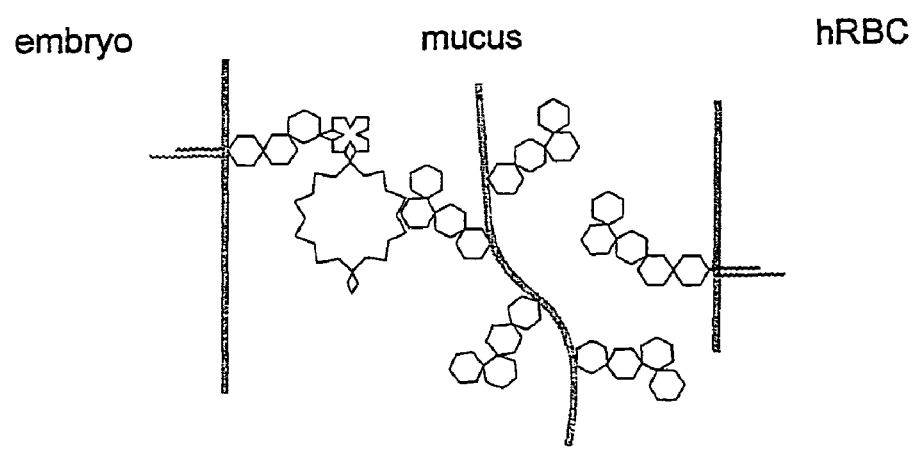

FIG. 9b— Schematic representation of BioUE transformed embryos (left) reacting with group O secretor mucus as determined by inhibition of reactivity of BioUE transformed embryos with group O red cells (human red cells—hRBC).

DETAILED DESCRIPTION

The following description of this invention relates primarily to the use of biotin/avidin binding. It is important to note that other combinations of attachment molecule and glycolipid modified to incorporate a binding part which allow high affinity conjugation (i.e. covalent or non-covalent bonding) between the attachment molecule and glycolipid are suitable.

Terms or expressions used to describe this invention are defined as follows:

i. endometrium— The tissue lining the internal surface of the uterus. It is this layer of epithelial cells and extracellular matrix (i.e. mucus) that the implanting embryo comes into first contact with. The epithelial and underlying stromal cell layer cyclically thickens, secretes mucus and is shed from the body under the hormonal influence of the menstrual cycle.

Attachment to the endometrium lining may be by interaction between the attachment molecule and one or more components of the endometrium, including membranes of the epithelial cells, mucus, mucin components of the mucus, or an exogenously introduced component of the mucus.

ii. zona pellucida— The glycoprotein coat that surrounds the mammalian oocyte (egg) and embryo from the 1-cell to blastocyst (6 day old) stage of development. Prior to embryo attachment and implantation, the zona pellucida is shed from the embryo by a number of mechanisms including proteolytic degradation. The zona pellucida functions initially to prevent entry into the oocyte by more than one sperm, then later to prevent premature adhesion of the embryo before its arrival into the uterus.

iii. attachment molecule— Any carbohydrate or oligosaccharide, glycolipid, glycoconjugate, protein or synthetic molecule that can interact with one or more components of the targeted tissue (e.g. endometrium) to localise the attachment molecule to the tissue. Desirably the attachment molecule will interact with endometrium and not the embryo.

The attachment molecule may be selected from natural or synthetic carbohydrates or oligosaccharides, glycolipids, glycoconjugates proteins, peptides, antibodies, lectins, polymers such as polyvinyl pyrrolidine, a1d functionally equivalent derivatives thereof.

iv. glycolipid— Any lipid-containing carbohydrate, including phosphoglycerides (e.g. glycosylphosphatidylinositol) and sphingolipids (e.g. glycosyl ceramides, cerebroside sulphate, and gangliosides).

v. binding part— The portion of the attachment molecule or of the glycolipid that interacts (or docks) with the attachment molecule or glycolipid respectively, or with a bridging molecule, to provide a non-covalent or covalent bond between the binding part and the attachment molecule, glycolipid, or bridging molecule, thereby providing a glycolipid-attachment molecule construct.

vi. bridging molecule— a molecule that links the binding part of the glycolipid with the binding part of the attachment molecule. For example, avidin (interacting with biotin on either the glycolipid or the attachment molecule), or a chelator (interacting with a poly-histidine).

vii. biotin— Biotin is a water-soluble vitamin (H). It consists of fused imidazolinone and thiophan rings with a pentanoate side-chain attached to the latter. Biotin has an extremely high affinity to bind the protein avidin via its imidazolidine ring. The use of the term "biotin" in the description is intended to be understood to include derivatives of biotin with functional equivalence.

viii. avidin (Av)— Avidin derived from chicken egg white is a glycoprotein with a molecular mass of 67 kDa. It contains four identical sub-units, each bearing a biotin-binding site. The use of the term "avidin" in the description is intended to be understood to include derivatives of avidin with functional equivalence.

ix. Chelation— Chelation is defined as the strong binding that occurs between chelated metal ions and proteins. Certain chemical groups called ligands, such as iminodiacetate and nitrilotriacetate, form a stable metal coordination complex (or metal chelate) with a divalent transition metal ion eg $Ni^{2+}$, $Co^{2+}$ or $Cu^{2+}$. Peptides containing poly-histidine residues strongly bind to such a metal chelate by participation of imidazole side-chains in chelation.

x. BioG (Biotinylated glycolipid)— Biotin coupled to a glycolipid.

xi. BiolgG (Biotinylated Immunoglobulin G)— Biotin coupled to immunoglobulin G. When the antibody has specificity this is indicated as a superscript. For example BiolgG$^D$, BiolgG$^{Aleb}$, BiolgG$^{A,B}$ and BiolgG$^{Lab}$ are biotinylated antibodies directed against the D, ALe$^b$, AB and Le$^b$ antigens respectively.

xii. Lectin— is a sugar-binding protein of non-immune origin that agglutinates cells or reacts with glycoconjugates.

Glycolipids can insert into cell membranes without damaging cells. The invention provides for the insertion of synthetic molecules (including exogenously prepared glycolipid-attachment molecule constructs) into the glycoprotein coat of early embryos (zona pellucida) and the lipid bi-layer membrane of embryo cells that are involved in embryo implantation.

While this technology is applicable to embryo implantation in a wide variety of animals, it is most relevant to humans. However, this invention is not limited to human embryo modification and implantation. In particular inter species transfer, embryo modification and implantation is contemplated.

One or several intercellular interactions can be targeted for improvement using the technology of this invention. This may be a direct adhesion mechanism, or other mitotic stimulus or cell recognition events. While the attachment molecule and glycolipid may be derived from natural or synthetic sources, the assembly of the attachment molecule and the glycolipid is synthetic i.e. performed at least in part exogenously. The covalent or non-covalent, direct or indirect, attachment of the attachment molecule to the glycolipid may occur either before or after the insertion of the glycolipid into the cell membrane.

One combination that employs biotin/avidin binding is a biotinylated glycolipid as the primary insertion molecule, an avidin bridging molecule, and a biotinylated attachment molecule (in this case an antibody or lectin or carbohydrate). The insertion process operates by exploiting the high binding affinity of avidin for biotinylated molecules, essentially forming a sandwich complex. Firstly, the biotinylated glycolipid is inserted into the cell membrane to provide an anchor for the application of subsequent molecules. Secondly, the inserted cell membrane is treated with avidin that binds to the biotinylated glycolipid. The final phase involves conjugation of the inserted molecules with the biotinylated endometrial adhesion molecule. To demonstrate this invention, the attachment molecules are the immunoglobulin G antibody, a lectin (*Ulex europeaus*) and glycolipid. However, it must be emphasised that these molecules could be substituted by any one of a variety of natural or synthetic molecules.

Immunoglobulin G and lectin were chosen for development of the invention because of the ease in which molecular insertion and cell adhesion between two cell types can be confirmed using serological techniques. Preliminary development and proof of principle for each phase of the invention was carried out using human RBCs. Essentially the red cell membrane is a fluid membrane not too dissimilar to the embryo membrane, but much easier to obtain and handle. Thereafter, the insertion technique was tested on mouse embryos ranging from the 2-cell to blastocyst stage of development.

At each developmental phase, it was important to investigate the potential risk of detrimental effects of the invention on embryonic development and maternal health. Initially, the morphological development of treated embryos was compared with control embryos cultured in vitro. The outcome of normal live births from transferred treated embryos into recipient mice provides evidence of the safety of the invention. Finally, the ongoing reproductive performance of the treated offspring proves that no lasting detrimental effects are present.

There are several steps in the practice and demonstration of the utility of this invention;

Inserting natural glycolipids which may be potential adhesion/communication molecules into embryo membranes (in particular thorough carbohydrate-carbohydrate interactions, or through carbohydrate-protein interactions);

Inserting modified (biotinylated) glycolipids in embryo membranes as a mechanism to attach biotinylated molecules through an avidin bridge;

Attaching IgG membrane/mucus adhesion molecules to embryo membranes;

Attaching lectin membrane/mucus adhesion molecules to embryo membranes;

Proving the embryo is unharmed by the processes above.

Adhesion of embryo's to cell membranes was proven initially by reactivity against red cells and secondarily against endometrial cells. For all intents and purposes red cells are equivalent to endometrial cells as they are of a similar size and are both fluid membranes. In some instances red cells were considered as being "surrogate" endometrial cells. A serological technique known as rosetting (Indiveri et al 1979), was used to demonstrate the adhesive capacity of the embryo's which had been modified with adhesive proteins (eg antibodies or lectins) with other cells. This was either done directly where the attached binding protein reacted with the corresponding antigen on the red/endometrial cells or through a bridge such as anti-IgG. In this way it was possible to prove that not only had the adhesion molecule been successfully inserted into the embryo, but that an artificial adhesion between two cell types had been created. For the purposes of demonstration the specificity of the antibodies selected were those chosen to react with red cells, or for which glycolipid antigens existed which could be inserted into cells to make them express the desired antigen. In the actual application of this technology red cell specific antibodies/lectins would be replaced with antibodies that detect antigens on the endometrial cells and/or mucins. The specificity of the antibodies or lectins which can be used is limited only by availability.

In order to insert molecules into cell membranes biotinylated glycolipids (BioG; Example 1) and biotinylated antibodies (BiolgG; example 2) had to be prepared (when they could not be purchased). The insertion phenomenon using BioG and avidin concentrations were optimised using red cells (example 3).

Insertion Media

Stock glycolipids for insertion were prepared in a solvent free saline (see Example 4) to ensure protection from the reported detrimental effects of alcohols in sensitive embryonic cells (Lau et al. 1991). The stock solution containing saline suspended (micelles) of glycolipids was diluted in various cell culture media or saline for insertion experiments. The results in Example 5, are in agreement with other investigators that the presence of serum, plasma or detergents is unnecessary for insertion to occur (Zhang et al. 1992). In contrast with previous reports, the presence of albumin in the M2 media in Example 5, does not impede the insertion process. Therefore, the insertion solution is effective in culture media with and without the presence of protein. Examples 6, 7 and 8 clearly demonstrate successful insertion of glycolipids into endometrial cells and embryo's.

Inserting natural glycolipids which may be potential adhesion/communication molecules into embryo membranes (in particular through carbohydrate-carbohydrate interactions, or through carbohydrate-protein interactions).

It is well established that cells can communicate through the low avidity binding characteristics of carbohydrate-carbohydrate interaction. These low affinity reactions are believed to be involved in cellular communication and adhesion (Bovin, 1996; Hakomori 1996; Mikhalehik et al 2000; Wang et al 2001). Natural glycolipids can be added to the surfaces of embryo and endometrial membranes, thus modifying their carbohydrate expression (examples 6 and 7). Such modified cells may then potentially be available to react either with reactive carbohydrates expressed on the endometrial lining (membrane or mucus) or may react with carbohydrate reactive proteins expressed on the endometrial surfaces.

Inserting Modified (Biotinylated) Glycolipids in Embryo Membranes as a Mechanism to Attach Biotinylated Molecules through an Avidin Bridge Like the natural glycolipids (examples 6 and 7) biotinylated glycolipids are able to be inserted into the embryo membranes including the zona pellucida (example 8).

The biotinylated ganglioside once inserted into the membrane is able to be reacted with avidin, which can then pick up biotinylated molecules, thus modifying the surface of the embryo (examples 9-14).

Attaching IgG Membrane/Mucus Adhesion Molecules to Embryos Membranes

Several mechanisms were examined to show the attachment of IgG adhesion molecules to cell membranes. These included direct attachment of an antibody which could react with the membrane of another cell for example red cells (examples 9 and 10) and endometrial cells (example 12). Example 9 demonstrates the direct rosetting method, with an antibody specific to the red cell protein antigen D. Alternatively a multistage adhesion can be induced where some components are added to the embryo and others to the cell for adhesion. This can be seen in Example 10, where the carbohydrate specific IgG attachment molecule BiolgG$^{A,B}$, was inserted into RBCs which adhered to embryos expressing the reactive antigens. An alternative interaction was also demonstrated, where embryos were coated with BiolgG$^{A,B}$, and were shown to complex with RBCs inserted with BioG-avidin.

Additionally a bridging molecule such as anti-IgG could also be used to bridge IgG attached to both the membranes of the embryo and another cell, in this case red cells (example 11) which it is desired the embryo attaches to. In this example, (example 11), human anti-D sensitised RBCs were used to demonstrate the adhesive properties of embryos inserted with BiolgG, an immunoglobulin G with no specificity to any known antigen. Addition of anti-IgG to the BiolgG embryos and anti-D sensitised RBCs caused indirect resetting between the two cell types. Ideally an antigen, which is expressed on endometrial cells but is absent on the embryo, would be an appropriate antibody target. In the absence of easy availability of such a reagent and also to demonstrate a further potential application, we inserted antigens into the endometrial cell membrane for which a a biotinylated antibody was available. These inserted antigens become integral parts of the cell membrane and as such can be considered part of the membrane (example 6). Blood group antigens Le$^b$ and ALe$^b$ were added to endometrial cells and the corresponding biotinylated antibodies were attached to embryo's via BioG-avidin (example 12). The attachment of the endometrial cells to the embryo's proves the mechanism of modified embryo induced adhesion. Additionally this process opens up the opportunity to both insert molecules into the embryo and the recipient (e.g. lavage) to induce/enhance adhesion between the embryo and the recipient.

These various examples illustrate the use of IgG that can target either carbohydrate or protein antigens as attachment molecules for various cell membrane attachment interactions.

Attaching Lectin Membrane/Mucus Adhesion Molecules to Embryos Membranes

Lectins are non-immunological carbohydrate binding proteins. In example 13, the biotinylated lectin *Ulex europaeus* (BioUE) was inserted into embryos to demonstrate a direct adhesive interaction with group C RBCs bearing the H type 2 carbohydrate antigen (specific antigen for UE). Additional the same phenomenon can be demonstrated with binding to endometrial cell culture (example 14)

Because the mucins will cover endometrial cells in utero the ability to modify the embryo to react with antigens on mucus was also demonstrated. Lectins were used for this purpose but antibodies reactive with mucus would be equally as applicable. In example 13 *Ulex europaeus* modified embryos were reacted with H type 2 containing mucus (obtained from human group O salivary secretions). In an inhibition assay the addition of H type 2 bearing mucus inhibited red cell rosette formation, illustrating that mucus had bound to the UE inserted embryos thus preventing the lectin reacting with red cells.

Proving the Embryo is Unharmed by the Processes Above.

An essential requirement of any implantation therapy is that it must not induce any detrimental effects on the normal fetal growth of the treated embryo, or the off spring, or the mother. Preliminary experiments with BioG inserted embryos showed no difference in morphology or zona hatching rate from control embryos during 5 days of in vitro culture (Example 15). Similarly, no difference from control embryos was noted (although not subjected to statistical analysis) between the pregnancy, live birth rate and normalcy of offspring in treated embryos (BioG, BioG/Av/BiolgG, ZI and ZF) when transferred into recipient mice (Example 16 and Example 17). Ultimately, the ongoing fertility rate and second generation pups of the offspring resulting from treated embryos was apparently normal (Example 18).

EXAMPLES

Example 1

Biotinylated gangliosides (BioG) were prepared using a modified procedure described by Wilchek and Bayer (1987). The extraction and purification of porcine gangliosides is carried out using established techniques (Karlsson 1987, Ladisch et al. 1987, Ledeen et al. 1982).

1. Dried gangliosides purified from porcine brains, were reconstituted in PBS with the aid of sonification.
2. The ganglioside sialic residues were oxidized by the addition of sodium m-periodate.
3. The solution was subjected to 24 hr dialysis to remove the resulting peroxide.
4. The oxidised ganglioside was incubated with biotin amidocaproyl hydrazide (Sigma B-3770) for 1 hr.
5. The solution was subjected to further overnight dialysis in water to remove excess biotin amidocaproyl hydrazide.
6. The resulting solution was dried via rota evaporation and reconstituted in 50% methanol water. Further evaporation was performed under nitrogen gas in a reduced pressure desiccator overnight.

Example 2

Biotinylated immunoglobulin G was prepared using a method described by O'Shannessy 1990). Using similar procedures to those outlined in Example 1, the IgG was oxidised with a periodate solution and incubated with biotin amidocaproyl hydrazide.

Example 3

Optimum BioG insertion concentrations and conditions were established by labelling the inserted BioG RBCs with avidin-FITC. The results are outlined in Table 1.

TABLE 1

Fluorescent signal of human RBCs inserted with a range of BioG and labelled with avidin-FITC concentrations.

| Avidin-FITC | BioG mg/ml | | | |
|---|---|---|---|---|
| mg/ml | 10 | 5 | 2.5 | 0 |
| 0.90 | ++++ | ++++ | +++ | − |
| 0.45 | ++++ | ++++ | +++ | − |
| 0.33 | ++++ | ++++ | +++ | − |
| 0.16 | ++++ | ++++ | +++ | − |
| 0 | − | − | − | − |

The optimum insertion concentration of BioG was 5 mg/ml. The minimum concentration of avidin required for adequate detection of BioG at 5 mg/ml concentration, was 0.16 mg/ml. The optimum minimum insertion time was determined to be 1 hour as seen in Table 2.

TABLE 2

Fluorescent signal of human RBCs incubated with BioG for a variety of times, then labelled with avidin-FITC.

| Hours of incubation | | | | | | | | |
|---|---|---|---|---|---|---|---|---|
| 0.25 | 0.5 | 0.75 | 1 | 1.5 | 2 | 4 | 6 | 26 |
| +++ | +++ | +++ | ++++ | ++++ | ++++ | ++++ | ++++ | ++++ |

The amount of fluorescent signal score for the 2 hr incubation tube reduced from 4+ to 3+ after avidin labelling 5 days post insertion, suggesting minimal loss of inserted molecules over time.

Example 4

Stock glycolipids for insertion were prepared in solvent free saline to protect sensitive cells such as embryos from solvent exposure during insertion treatment.
1. Purified dried glycolipids (e.g. Le$^b$, A, or biotinylated gangiloside) were dissolved in a glass tube with 50% methanol/water to give a 10 mg/ml solution.
2. The solution was filtered with a 0.22 micron solvent resistant filter into a sterile glass tube.
3. A 150 μl aliquot of the solution was marked on the side of the glass tube to indicate the end point of evaporation. A further 850 μl aliquot was placed in the glass tube to give a total of 1 ml (containing 10 mg).
4. The tube was placed under a gentle stream of nitrogen gas in a dry heat block at 50° C. until the meniscus was reduced to the marked evaporation line.
5. The solution was made up to 200 μl with a balanced salt solution of sterile PBS by adding 20 μl of 10× phosphate buffered saline (PBS) and 30 μl of 18 mΩ water.
6. The final 50 mg/ml solution was aliquoted into sterile microcentrifuge tubes and frozen at −70° C. or freeze dried (to be later reconstituted with water).
7. Samples from the stock solution were then taken for dilution in cell culture media for transformation experiments.

Example 5

The requirement for plasma or serum in the insertion media was shown not to be necessary. The ability for fluorescein-isothiocyanate-labelled avidin-(avidin-FITC Sigma A-2901) to bind to biotin formed the basis of detecting inserted BioG in RBCs when viewed under microscope fluorescence at 470 nm. In this study, a comparison in the degree of fluorescent signal in avidin-FITC treated BioG human RBCs was carried out for insertion solutions in a variety of tissue culture or serology media.
1. 5 μl of packed RBCs were mixed with 30 μl of 2 mg/ml BioG (final conc. 12 μg/ml of packed RBCs) in one of the following aqueous media for 2 hrs at 37° C. with frequent mixing. The range of aqueous media included: Celpresol (CSL Biosciences, Australia), M2 media mouse embryo handling media (Sigma M5910), SQC mouse culture media (Vitrolife, Sweden), Medicult human embryo culture media (Medicult Denmark) and PBS (made in-house).
2. The RBCs were washed 3× in saline by centrifugation and incubated with 9.5 μl of avidin-FITC for 1 hr at 37° C.
3. The cells were washed 3× in saline and viewed under a fluorescent microscope at 470 nm.

The concentrations and fluorescent microscopy results are outlined in Table 3.

TABLE 3

Fluorescent signal of human RBCs inserted with BioG and labelled with Avidin-FITC

| Insertion media | Celpresol albumin - free | PBS albumin - free | SQC albumin - free | M2 albumin 10% | plasma |
|---|---|---|---|---|---|
| Experimental | +++ | ++ | +++ | ++++ | ++ |
| Negative Controls | − | − | − | − | − |

The presence of a clear fluorescent signal in both M2 and SQC cell culture media deemed them to appropriate for routine embryo insertion experiments.

Example 6

The ability of natural glycolipids to insert into cell membranes was tested by inserting glycolipid A into endometrial cells. Insertion was confirmed by labelling with anti-A then by secondarily labelling with anti-mouse immunoglobulin conjugated to fluoresceinisothiocyanate (anti-mouse Ig-FITC) and detected by fluorescent microscopy.

A 5 million/ml heterogeneous solution of murine endometrial cells was prepared by dissecting the uterine horn, scraping out the endometrial tissue, and incubating the tissue at 37° C. for 1.5 hrs in 500 μl of 0.25% pronase and 1 ml of 0.5% collagenase. After incubation the cells were washed and suspended in DMEM-F12 culture media Glycolipid A was inserted and detected in endometrial cells using the following method:
1. Freeze dried glycolipid A was resuspended in DMEM-F12 to give a 10 mg/ml and a 1 mg/ml solution.
2. Three micro-centrifuge tubes were prepared each containing a 50 µl solution of 5 M/ml endometrial cells. The following reagents were added to each micro-centrifuge tube a) 50 µl glycolipid A (10 mg/ml), b) 50 µl glycolipid A (1 mg/ml) and c) 50 µl CMF(calcium magnesium free)-HBSS. The cells were incubated overnight at room temperature.
3. After each treatment step the endometrial cells were washed 3 times by resuspending in M2 media and centrifuging at 2000 rpm for 3 minutes. The washed cells were then resuspended in 50 µl of M2 media.
4. Endometrial cells were subsequently reacted with anti-A by adding 50 µl of anti-A murine monoclonal antibody to each micro-centrifuge tube and incubating at room temperature for 30 minutes.
5. To test the presence by fluorescence 10 µl of mouse anti-Ig FITC was added to each micro-centrifuge tube containing the washed cells and incubated in dark conditions at room temperature for 30 minutes.
6. Endometrial cells were mounted on glass slides and viewed under a fluorescence microscope using a 470 nm filter and photographed at 200-400× magnification.
7. The results of the experiment is outlined in Table 4

TABLE 4

Fluorescent signal of murine endometrial cells inserted with blood group A glycolipids.

| Insertion glycolipid | Fluorescence |
|---|---|
| Glycolipid A 10 mg/ml | ++++ |
| Glycolipid A 1 mg/ml | +++ |
| Negative Control | − |

Example 7

The ability of natural glycolipids to insert into cell membranes was tested by inserting natural glycolipids A and $Le^b$ separately in murine embryos.

Glycolipid A and $Le^b$ were inserted into the cell membranes of zona pellucida free (ZF) murine embryos from blastocyst to hatched blastocyst stage. The insertion was confirmed by labelling with anti-A or anti-$Le^b$ respectively, then by secondarily labelling with anti-mouse immunoglobulin conjugated to fluoresceinisothiocyanate (anti-mouse Ig-FITC) and detected under fluorescent microscopy.

Embryo insertion was performed in both M2 (Sigma M5910) and SQC (Vitrolife, Sweden) media using the following method:
1. Super-ovulated mouse embryos on day 3.5 post coitus were obtained as described in Example 16.
2. Embryos from each mouse were stored in sterile micro-centrifuge tubes with M2 media.
3. Culture dishes were prepared with 3×50 µl micro-drops of media overlaid with mineral oil.
4. Embryos with zonas intact (ZI) were placed in 0.25% pronase (Sigma P8811) in CMF-HBSS media for 6 minutes at 37° C. until the zona had disappeared. All embryos were zona free (ZF).
5. All embryos were washed 3 times in M2 media after each treatment step by placing them into a fresh 100 µl drop of media using a pulled glass capillary tube and syringe.
6. The following reagents were added to separate SQC micro-drops: a) 50 µl Glycolipid A (10 mg/ml), b) 50 µl Glycolipid $Le^b$ (5 mg/ml) and c) 50 µl M2 media. Equal numbers of ZF embryos were placed in the micro-drops in a 5% $CO_2$, 37° C. incubator for 120 minutes.
7. Embryos were subsequently cultured in a corresponding binding antibody for each glycolipid. The following reagents were added to separate micro-drops: a) 40 µl anti-A murine monoclonal, b) 40 µl anti-$Le^b$ murine monoclonal and c) 40 µl anti-A murine monoclonal. The embryos from each group were placed in the SQC micro-drops and returned to the 5% $CO_2$, 37° C. incubator for 30 minutes.
8. Embryos were transferred to a SQC micro-drop containing 20 µl anti-mouse Ig-FITC and cultured in the drop for 1 hr in dark culture conditions (in 5% $CO_2$, 37° C.).
9. Embryos were mounted on a glass microscope slide in a 2 µl drop of media and overlaid with 2 µl of mineral oil.
10. The slides were viewed under a fluorescent microscope using a 470 nm filter and photographed at 20-40× magnification.

The results of each experiments performed are outlined in Table 5.

TABLE 5

Fluorescent signal of murine embryo's inserted with glycolipids A and $Le^b$ and labelled with anti-A or anti-$Le^b$ respectively, then secondarily labelled with anti-murine Ig FITC

| Insertion glycolipid | $Le^b$ glycolipid inserted | A glycolipid inserted |
|---|---|---|
| Experimental | ++ | ++++ |
| Negative Controls | − | − |

Example 8

Insertion of biotinylated gangliosides (BioG) into the cell membranes of both zona pellucida intact (ZI) and zona pellucida free (ZF) murine embryos from 2-cell stage through to hatched blastocyst stage was confirmed by a positive signal of avidin conjugated to fluoresceinisothiocyanate (avidin-FITC) detected under fluorescent microscopy. Some ZI embryos underwent zona removal post BioG insertion and pre avidin-FITC treatment to clearly visualise the degree of BioG insertion in the cell membrane. Embryo insertion was performed in both M2 (Sigma M5910) and SQC (Vitrolife, Sweden) media using the following method:
1. Collection of super-ovulated mouse embryos on day 1.5 to day 3.5 post coitus was performed as described in Example 16.
2. Embryos from each mouse were split equally between control and experimental groups where possible and transported from the animal facility to laboratory in separate sterile microcentrifuge tubes with M2 media.
3. A culture dish was prepared with 50 µl micro-drops of media overlaid with mineral oil and the following reagents in separate drops: a) 5 µl of BioG (50 mg/ml stock), and b) 5 µl of avidin-FITC (1 mg/ml).
4. Embryos destined for ZF insertion treatment were placed in 0.5% pronase (Sigma P8811) in M2 media for 6 minutes at 37° C. until the zona had disappeared.

5. All embryos were washed 3 times in M2 media after each treatment step by placing them into a fresh 100 µl drop of media using a pulled glass capillary tube and syringe.
6. ZF and ZI embryos were placed in the BioG micro-drop for 1-2 hours under appropriate culture conditions.
7. A group of ZI embryos were treated with 0.5% protease prior to further treatment.
8. Embryos were subsequently cultured in the avidin-FITC drop for 1 hr in dark culture conditions.
9. Embryos were mounted on a glass microscope slide in a 2 µl drop of Citiflour (R1321, Agar Scientific, NZ) and overlaid with 2 µl of mineral oil, to replace the need for a cover-slip. A felt tip marker was used to circle the location of the specimen.
10. The slides were viewed under a fluorescent microscope at 250-500× magnification using a 470 nm filter.

The results are outlined in Table 6.

Example 9

Direct adhesion between an embryo and RBCs was demonstrated using the biotinylated IgG specific for the protein antigen D (BioIgG$^D$). In this example, D+ve human RBCs were shown to positively rosette to mouse zone free embryos inserted with BioG/Av/BioIgG$^D$. No resetting occurred on the surface of untreated mouse embryos nor those inserted with BioG/Av only.

Mouse zone free embryos were inserted with BioG/Av and BioIgG$^D$ using the following method:

1. Zona free day 3.5 mouse embryos were incubated at 37° C. for 1.5 hours in a 50 µl microdrop containing 5 µl of BioG (50 mg/ml), then washed 3× in M2 media.

TABLE 6

Fluorescent signal emitted from embryos inserted with BioG and conjugated with avidin-FITC. The data represents the results of six experiments carried out on embryos at different developmental stages from 2-cell to hatched blastocysts. Zona free (ZF) embryos were treated with pronase, while hatched blastocysts had autonomously lost the zona. Some embryos were treated with avidin-FITC after further culture post BioG insertion. Unhatched blastocysts and zona intact (ZI) embryos were BioG treated with the zona retained

| Expt | Embryonic stage | Outline | Result - fluorescent signal |
|---|---|---|---|
| I | 2-Cell embryos freshly retrieved | a) ZI M2 media controls<br>b) ZI M2 media experimental<br>c) ZI SQC media controls<br>d) ZI SQC media experimental | a) nil<br>b) cells +++ (zona ++++)<br>c) nil<br>d) cells +++ (zona ++++) |
| II | 4-Cell cultured from 2-Cell | a) ZF controls<br>b) ZF experimental<br>c) ZI controls<br>d) ZI experimental | a) nil<br>b) +++<br>c) nil<br>d) +++ |
| III | late morula cultured from 2-Cell | a) ZF control embryos<br>b) BioG then pronase<br>c) pronase then BioG | a) faint homogenous signal<br>b) ++ to +++<br>c) +++ to ++++<br>Clear signal for polar body regardless of treatment |
| IV | unhatched and hatched blastocyst cultured from 2-Cell | a) hatched controls<br>b) hatched experimental<br>c) unhatched controls<br>d) unhatched experimental<br>e) arrested embryos<br>all treated with BioG then avidin-FITC 24 hrs later | a) nil (except in atretic cells)<br>b) ++ (stronger in atretic cells)<br>c) nil except for atretic cells<br>d) cells +++ (zona ++++)<br>e) cells +++ (zona nil)<br>no difference in morphology between control and experimental 24 hrs post BioG |
| V | blastocyst to hatched blastocyst cultured from 2-Cell | a) ZI BioG and avidin-FITC day-6<br>b) ZI BioG day-2 with further culture then avidin-FITC day-6 | a) + cells (zona ++ to ++++)<br>b) + cells (zona ++ to ++++) |
| VI | unhatched blastocysts | BioG treatment 24 hours previous as unhatched blastocysts then avidin-FITC treated as hatching blast.s<br>a) pronase then avidin-FITC<br>b) avidin-FITC then pronase<br>c) avidin-FITC no pronase | <br><br><br><br>a) cells +++ to ++++<br>b) cells +++ to ++++<br>c) cells + (zona +++ to ++++) |

2. The embryos underwent a $2^{nd}$ conjugation step where they were exposed to 5 µl of avidin (1 mg/ml) in a 50 µl micro-drop of media for 60 minutes at 37° C., and washed.
3. Finally, the embryos were incubated in a 50 µl microdrop containing 25 µl of BiolgG$^D$ (titre 1:1000) for 1 hour at 37° C.
4. The embryos were washed 3× in M2 media and placed in a fresh well of M2 media ready for rosetting with D+ve human RBCs.

The results are outlined in Table 7.

TABLE 7

BioIgG$^D$ transformed mouse embryo rosette experiment. D +ve human RBCs adhere to mouse embryos that are transformed with BioIgG$^D$ (Exp. group 3). This demonstrates the ability for antibody transformed embryos to adhere to a protein antigen on surrogate endometrial cells. No RBC adhesion was observed in either negative control groups.

|  | Experimental group | | |
| --- | --- | --- | --- |
|  | 1 | 2 | 3 |
| Embryo configuration | untreated | BioG/Av | BioG/Av/BiolgG$^D$ |
| RBC type | D+ve | D+ve | D+ve |
| Rosetting | nil | nil | ++ |

Example 10

Direct adhesion between an embryo and RBC was demonstrated using the biotinylated IgG specific for the carbohydrate antigens A,B (BiolgG$^{A,B}$). In this example, two combinations of insertion were tested. In the first instance, BiolgG$^{A,B}$ inserted mouse RBC's were shown to rosette to mouse embryos that are known to express an antigen reactive with IgG$^{A,B}$. Additionally, mouse RBC's inserted with BioG and avidin only, positively adhered to mouse embryos sensitised (coated) with BiolgG$^{A,B}$.

Mouse RBCs were inserted with BioG/Av and BioG/Av/BiolgG$^{A,B}$ using the following method:
1. 5 µl of BioG (50 mg/ml) was added to 500 µl of 10% mouse RBCs in PBS (final conc. 5 µg/µl of packed RBCs) and incubated on a mixer at 37° C. for 1 hour. The cells were washed 3× in PBS and resuspended to 500 µl.
2. 50 µl of 1 mg/ml avidin was added to the BioG inserted RBC solution (final conc. avidin 0.1 mg/ml) and incubated on a mixer at 37° C. for 1 hour. The cells were washed 3× in PBS and resuspended to give a 10% solution of RBCs. These BioG/Av inserted cells were used to react with embryo's sensitised with BiolgG$^{A,B}$.
3. A 100 µL aliquot of BioG/Av inserted RBCs was mixed with 50 µl of BiolgG$^{A,B}$ (10 µg/10 µl of packed RBCs) and incubated on a mixer at 37° C. for 1 hour. The cells were washed 3× with PBS ready for the rosetting with the embryos. These BioG/Av/BiolgG$^{A,B}$ inserted cells were used to react directly with embryos.

Mouse embryos were sensitised with IgG$^{A,B}$ using the following method:
1. ZF and ZI day-3.5 embryos were incubated in a microdrop of 25 µl of M2 media and 25 µl of BiolgG$^{A,B}$ (final conc. 0.1 mg/ml) for 1 hour at room temperature.
2. These BiolgG$^{A,B}$ sensitised embryos were washed 2× in M2 media and placed in a fresh well of M2 media ready for rosetting by exposure to the BioG/Av inserted mouse RBCs.

The results are outlined in Table 8.

TABLE 8

Embryo BioIgG$^{A,B}$ rosette experiment. Group 1 ZF embryos rosette with BioG/Av/BioIgG$^{A,B}$ mouse RBCs. Group 2 ZF and ZI embryos sensitised with BioIgG$^{A,B}$ rosette with BioG/Av transformed RBCs. Group 3 embryos represent a negative control and fail to rosette with BioG/Av transformed RBCs.

|  | Experimental Group | | |
| --- | --- | --- | --- |
|  | 1 | 2 | 3 |
| mRBCs configuration | BioG/Av/BioIgG$^{A,B}$ | BioG/Av | BioG/Av |
| embryo configuration | untreated | BioIgG$^{A,B}$ treated | untreated |
| ZF binding | +++ | +++ | − |
| ZI binding | − | ++ | − |

A grade from nil to 4+ was allocated to each group of embryos:
nil no binding
+ <10 RBCs
++ 10-20 RBCs
++++ >50 RBCs Example 11

The ability of modified embryos to adhere (through an immunological bridge) to antigens on other cell types was tested. In this example, the adhesion molecule was classified as biotinylated non-specific IgG and anti IgG [BiolgG+anti-IgG] which was conjugated in a third step to the inserted molecules BioG and avidin, on the cell membranes and zona pellucida of murine embryos. To confirm the complete insertion of this complex, IgG sensitised RBCs were allowed to rosette. The IgG that is attached to the anti-D sensitised RBCs is used as an antigen for the adhesion molecule— thus the antibody coating on the cells essentially acts as a cell bound protein antigen. This model is considered an indirect demonstrative example of adhesion, because anti-IgG is required to complete the adhesive complex.

Insertion, conjugation and adhesion of IgG sensitised RBCs was carried out as follows:
1. Anti-D sensitised RBCs were made by incubating 400 µl of human serum containing human anti IgG with 200 µl of RhD+ve human RBCs for 1 hr at 37° C. The RBCs were then washed in Celpresol and made up to a 5% solution for the rosette technique.
2. All embryos were retrieved from super-ovulated mice at the 2-cell stage and entered into the experiment either on the day of retrieval or after 48 hours of cell culture in SQC media (late morula to blastocysts stage).
3. BioG insertion was performed on both zona intact and zona free embryos with either M2 or SQC used as the insertion media.
4. The embryos then underwent a $2^{nd}$ conjugation step where they were exposed to, 5 µl of avidin (1 mg/ml) in a 50 µl of micro-drop of media for 60 minutes at 37° C. in appropriate culture conditions for each media type (i.e. $CO_2$ or atmospheric).
5. The washed embryos underwent a 3rd conjugation with 5 µl of BiolgG (1 mg/ml) in a micro-drop of media for 30 minutes at 37° C., then washed.
6. The embryos were placed in a micro-drop consisting of 25 µl of M2 media and 25 µl of monoclonal anti-IgG for 30 minutes at 22° C.
7. The treated and control embryos were washed and placed in separate drops of M2 media. A stream of either 50% anti-D sensitised RBCs or 50% untreated D+ve RBCs were gently blown over the embryos using a pulled capillary pipette attached to a syringe.

8. After 10 minutes at room temperature, the embryos were gently transferred to fresh media micro-drops using a wide bore capillary pipette (170 μm diameter) and assessed for RBC adherence under an inverted microscope at 250× magnification through the central plane of focus. A grade from nil to 4+ was allocated to each group of embryos:

| | |
|---|---|
| nil | no binding |
| + | <10 RBCs |
| ++ | 10-20 RBCs |
| ++++ | >50 RBCs |

The results are shown in Table 9. The adhesion of large quantities of anti-D sensitised RBCs to embryos (2-cell to blastocysts) indicates positive insertion of Bio/AV/BioIgG and demonstrates the ability of transformed embryos to adhere. There was no difference in the adhesion score between M2 and SQC insertion media. The adhesion score was moderately greater in the zona intact embryos than the zona free embryos.

TABLE 9

Adhesion scores of BioG/Av/BioIgG transformed embryos when exposed to either anti-D sensitised or untreated group D +ve RBCs. Experiment I compares the adhesion in zona intact 2-Cells when steps were carried out in M2 or SQC media. Experiment II assesses adhesion in late morula (LM) to blastocyst (blast) stage zona intact embryos. Experiment III compares adhesion in LM-blastocyst zona intact and zona free.

| | Stage of embryos | Zona free Y/N | Embryo treatment type | RBCs | Adherence |
|---|---|---|---|---|---|
| Expt. I | 2-Cell | N | BioG/Av/BioIgG M2 media | D +ve | − |
| | 2-Cell | N | BioG/Av/BioIgG M2 media | anti-D sensitised | +++ |
| | 2-Cell | N | BioG/Av/BioIgG SQC media | D +ve | − |
| | 2-Cell | N | BioG/Av/BioIgG SQC media | anti-D sensitised | +++ |
| Expt. II | LM-Blast | N | BioG/Av/BioIgG | anti-D sensitised | ++++ |
| | LM-Blast | N | BioG/Av/BioIgG | D +ve | − |
| | LM-Blast | N | Control untreated | anti-D sensitised | − |
| | LM-Blast | N | Control untreated | D +ve | − |
| Expt. III | LM-Blast | N | BioG/Av/BioIgG | anti-D sensitised | +++ |
| | LM-Blast | N | Control untreated | D +ve | − |
| | LM-Blast | Y | BioG/Av/BioIgG | anti-D sensitised | ++ |
| | LM-Blast | Y | Control untreated | D +ve | − |

Example 12

Carbohydrate antigens and anti-carbohydrate binding antibodies were utilised to demonstrate adhesion between embryo and endometrial cells. In this example both embryo and endometrial cells were modified with corresponding binding molecules (IgG antibodies directed against carbohydrate antigens and antibody reactive glycolipid antigens).

Two series of insertion were tested. In the first the biotinylated antibody directed against the $ALe^b$ antigen (Biolg-$G^{ALeb}$) was prepared (example 2) and inserted into embryo cell membranes via the BioG/avidin bridging mechanism while endometrial cell membranes were modified with the corresponding glycolipid $ALe^b$ antigen. In the second combination biotinylated antibody directed against the $Le^b$ antigen (BiolgG$^{Leb}$) was inserted into the embryo cell membranes via the BioG/avidin bridge while endometrial cell membranes were modified with the $Le^b$ glycolipid antigen.

Glycolipid modified endometrial cells were shown to adhere to the antibody modified embryos.

Murine endometrial cells were prepared as follows;

1. A 5-10 million/ml heterogeneous solution of murine endometrial cells was prepared as described in example 6.
2. Three micro-centrifuge tubes each containing 50 μl of 5-10 million/ml endometrial cells were prepared. The following reagents were added to separate tubes a) 50 μl $ALe^b$ glycolipid (5 mg/ml) b) 50 μl $Le^b$ glycolipid (5 mg/ml) and c) 50 μl DMEM-F12. All cells were incubated overnight at room temperature to allow the glycolipid molecules to insert.
3. The endometrial cells for the $ALe^b$ experiment were treated with a fluorescent stain by adding 10 μl of acridine orange/ethidium bromide solution to a 50 μl of endometrial cells. All cells were incubated in dark conditions at 37° C. for 30 minutes. This fluoro'chrome staining of the endometrial cells prior to embryo contact assists in identifying endometrial cells adhered to embryos by fluorescent microscopy.
4. The endometrial cells were washed 3 times by suspending in CMF-HBSS and centrifuging at 2000 rpm for 3 minutes.

Mouse zona free embryos were inserted with BioG/Av and BiolgG$^{ALeb}$ or BiolgG$^{Lab}$ using the following method:

1. Collection of super-ovulated mouse embryos on day 3.5 post coitus was performed as described in Example 16.
2. Micro-drop culture dishes were prepared with 50 μl of M2 media overlaid with mineral oil.
3. Embryos from each mouse were placed in SQC media microdrops and incubated in a 5% $CO_2$, 37° C. incubator overnight.
4. Embryos with zonas intact were placed in 0.25% pronase in CMF-HBSS media for 6-8 minutes until the zona had disappeared.
5. All embryos were washed 3 times in M2 media after each treatment step by placing into a fresh drop of M2 media using a pulled glass capillary tube and syringe.
6. Zona free day 4.5 experimental mouse embryos were incubated at 37° C. for 1.5 hours in a 50 μl SQC microdrop containing 5 μl of BioG (50 mg/ml).
7. The experimental embryos underwent a second conjugation step where they were exposed to 5 μl of avidin (1 mg/ml) in a 50 μl micro-drop of media for 60 minutes at 37° C.
8. Finally, the experimental embryos were split into two groups. Group 1 were placed in a 50 μl micro-drop containing 25 μl of BiolgG$^{ALeb}$ at 5 mg/ml. Group 2 in a 50 μl micro-drop containing 25 μl of BiolgG$^{Lab}$ at 5 mg/ml. Embryos were incubated for 1 hour at 37° C.

BiolgG$^{ALeb}$ and BiolgG$^{Lab}$ transformed mouse embryos were subsequently immersed in the corresponding modified endometrial cells to test for attachment in a two step process.

1. Micro-centrifuge tubes were prepared with the following: a) acridine orange stained $ALe^b$ glycolipid modified endometrial cells into which was placed BioG/Av/BiolgG$^{ALeb}$ inserted embryos; b) unstained Le$^b$ glycolipid modified endometrial cells into which was placed BioG/Av/BiolgG$^{Leb}$ inserted embryos.

2. The tubes containing the endometrial cells and embryos were gently mixed for 30 minutes at 37° C. Contents of each micro-centrifuge tube were transferred to a 4 well culture plate.
3. Embryos were carefully removed from the wells and mounted on glass slides. Embryos were viewed under a fluorescence microscope and photographed at 200-400× magnification.

The results are outlined in Table 10

TABLE 10

Degree of attachment of ALeb and Leb glycolipid inserted endometrial cells to murine embryo's inserted with BioG/Av/BioIgGALeb and BioG/Av/BioIgGLeb respectively.

| | Modifications to embryos and endometrial cells | |
|---|---|---|
| | Embryo: BioG/Av/BioIgG$^{ALeb}$ Endometrial cells: ALe$^b$ + AcOr | Embryo: BioG/Av/BioIgG$^{Leb}$ Endometrial cells: Le$^b$ |
| Cell attachment observed in bright field | ++ | ++ |
| Cell attachment observed under fluorescence | +++ | ND |

AcOr = fluorochrome acridine orange
Cell attachment scoring; + = 1-4 cells, ++ = 5-10 cells per embryo, +++ > 10 cells per embryo
ND = Not Done Example 13

The adhesive properties of *Ulex europaeus* inserted mouse embryos, was confirmed by direct adhesion to group O human RBCs by resetting. *Ulex europaeus* is a lectin that binds specifically to the carbohydrate antigen H type 2 present on the surface of group O human RBCs and in the mucus/saliva of group O individuals expressing the secretor phenotype. Adhesion of UE transformed embryos to secretor mucus was also demonstrated by the inhibition of rosetting with group O RBCs after prior exposure to the mucus.

Insertion and conjugation of embryos with UE was conducted as follows:

1. The zona pellucidae were removed from embryos by incubating in a 100 μl microdrop of 0.25% pronase in M2 media at 37° C. for 6 minutes, then washed 3× in M2 media.
2. Embryos were incubated in a 50 μl microdrop of SQC media containing 5 μl of 50 mg/ml BioG (final conc. 0.2 mg/ml) for 1.5 hrs at 37° C.
3. The washed embryos were incubated in a 50 μl microdrop of SQC media containing 5 μl of avidin 1 mg/ml (final 0.1 mg/ml) for 1 hr at 37° C., then washed 3× in M2 media.
4. Finally the embryos were incubated in a 50 μl microdrop of SQC media containing 25 μl of BioUE 100 μg/ml (final conc. 50 μg/ml) for 40 minutes at 37° C. After washing 3× in M2 media, the embryos were placed in a fresh drop of M2 media, in preparation for RBC resetting.
5. Group 3 and group 4 BioUE inserted embryos were incubated for 30 minutes at RT in a 50 μl drop of a 1:10 dilution of secretor and non-secretor mucus (respectively). The embryos were placed in a fresh drop of M2 media without washing in preparation for RBC resetting.
6. All untreated, treated and mucus pre-exposed groups of embryos, had a stream of group O RBCs gently aspirated around them. After 10 minutes incubation at RT, the embryos were carefully transferred to a fresh drop of M2 and the degree of RBC attachment was observed under an inverted microscope as described in Example 11.

The results are outlined in Table 11.

TABLE 11

Ulex europaeus transformed mouse embryo rosette and mucus inhibition experiment. Group O (H type 2 bearing) RBCs adhere to mouse embryos that are transformed with UE (Exp. group 2). This adhesion is inhibited by pre-exposure to O secretor H type 2 bearing mucus (Exp. group 3 -) but not by O non-secretor mucus (Exp. group 4) where the H type 2 antigen is absent.

| | Experimental group | | | |
|---|---|---|---|---|
| | 1 | 2 | 3 | 4 |
| Embryo configuration | untreated | BioG/Av/BioUE | BioG/Av/BioUE | BioG/Av/BioUE |
| Mucus incubation | nil | nil | O secretor | O non-secretor |
| RBC type | O | O | O | O |
| Rosetting | nil | +++ | nil | +++ |

Cell attachment scoring + = 1-4 cells, ++ = 5-10 cells per embryo, +++ > 10 cell per embryo Example 14

In this example both embryo and endometrial cells were modified with corresponding binding molecules. The biotinylated lectin *Ulex europaeus* (BioUE) was inserted into embryo cell membranes via the BioG/avidin bridging mechanism (BioG/Av/BioUE). Endometrial cell membranes were modified with glycolipid H type 2 and stained with pyronine Y. Fluorochrome staining of the endometrial cells prior to embryo adhesion assists in identification of bound endometrial cells when visualised by fluorescent microscopy.

Modified endometrial cells were shown to adhere to UE transformed embryos. In comparison, minimal attachment on the surface of untreated mouse embryos was observed.

Endometrial cells were inserted with H type 2 glycolipid and stained with pyronine Y by the following method.

1. A 5-10 million/ml heterogeneous solution of murine endometrial cells was prepared (as per example 6).
2. Two microcentrifuge tubes were prepared each containing a 1 ml solution of 5-10 M/ml endometrial cells. The cells were subsequently centrifuged at 2000 rpm for 3 minutes before aliquoting the supernatant to leave 5 μl of packed endometrial cells in each tube. 100 μl of H type 2 glycolipid extracted from human group O red cell membranes (10 mg/ml) was added to the experimental group of endometrial cells and 100 μl of DMEM-F12 media added to the control group of endometrial cells. All cells were incubated overnight at room temperature.
3. After each treatment step the endometrial cells were washed 3 times by resuspending in CMF-HBSS media and centrifuging at 2000 rpm for 3 minutes.
4. Endometrial cells were treated with pyronine Y by adding 20 μl of pyronine Y (15 μg/ml) to each microcentrifuge tube and incubating at 37° C. in dark conditions. The cells were thoroughly washed.

Mouse zona free embryos were inserted with BioG/Av and BioUE using the following method:

1. Collection of super-ovulated mouse embryos on day 3.5 post coitus was performed as described in example 16
2. Micro-drop culture dishes were prepared with 50 µl of SQC media overlaid with mineral oil.
3. Embryos were placed in SQC media microdrops in 5% $CO_2$ and incubated 37° C. overnight.
4. Embryos with zonas intact were placed in 0.25% protease in CMF-HBSS media for 6-8 minutes until the zona had disappeared.
5. All embryos were washed 3 times in M2 media after each treatment step by placing into a fresh drop of M2 media using a pulled glass capillary tube and syringe. Embryos were split into experimental and control groups. The experimental embryos underwent the treatment outlined in steps 6-9; the control embryos were incubated in M2 media for the equivalent length of time.
6. Zona free day 4.5 mouse embryos were incubated at 37° C. for 1.5 hours in a 50 µl M2 micro-drop containing 5 µl of BioG (50 mg/ml).
7. The embryos underwent a second conjugation step where they were exposed to 5 µl of avidin (1 mg/ml) in a 50 µl micro-drop of media for 60 minutes at 37° C.
8. Finally, a micro-drop was prepared with 50 µl M2 and 25 µl of BioUE (1 mg/ml). Experimental embryos were placed in the micro-drop and incubated in for 1 hour at 37° C.

BioUE transformed mouse embryos were subsequently immersed in the modified endometrial cells to test for attachment in a two step process.
1. A 4-well culture dish was prepared with 2 wells each containing 50 µl of modified, and stained endometrial cells. Control embryos and modified embryos were inserted into separate wells and gently mixed for 30 minutes.
2. Embryos were carefully removed from the wells and mounted on glass slides. Embryos were viewed under a fluorescence microscope and photographed at 200-400× magnification.

The results are outlined in Table 12.

TABLE 12

Attachment of murine embryo's inserted with BioG/Av/BioUE to endometrial cells inserted with H type 2 glycolipids (from red cell membranes).

| | Modifications to embryos and endometrial cells | |
|---|---|---|
| | Embryo: BioG/Av/BioUE Endometrial cells: H type 2 + PY | Embryo: nil Endometrial cells: nil |
| Attachment | ++ | +/− |

PY = fluorochrome pyronine Y
Cell attachment scoring = + 1-4 cells, ++ = 5-10 cells, +++ > 10 cells per embryo
ND = Not Done Example 15

The viability of murine embryos following BioG insertion treatment was confirmed by continued culture and assessment of morphological development. Eleven 2-Cell mouse embryos underwent BioG insertion with subsequent wash steps and culture in a 50 µl micro-drop of SQC media overlaid with mineral oil. Sixteen control embryos were cultured in a separate micro-drop in the same 4-well culture dish (Nunc 176740). Forty-eight hours later there was no difference in morphology between the experimental and control embryos. All embryos had reached the expected late morula to early blastocyst stage of development. Equal numbers of embryos initiated zona hatching by Day 5 of culture.

Example 16

The viability of murine embryos treated with biotinylated ganglioside (BioG) was confirmed by the presence of implantation sites and live birth of pups after embryo transfer (ET) into recipient mice. The retrieval, treatment, and transfer of embryos were carried out on the same day at the animal facility. All embryo manipulations, molecular insertions and incubations were performed in M2 HEPES buffered media on a 37° C. heated microscope stage.

Donor Superovulation and Embryo Retrieval

Large and relatively predictable numbers of embryos can be collected for experiments by using fertility drugs to stimulate the ovaries of immature mice which are highly sensitised to follicle stimulating hormone (FSH).

Prepubescent (<35 day old) CBA/C57 F1 female mice were injected with 5IU of FSH (Folligon, Pharmaco, NZ) at 1700 and again 48 hours later with 5IU of human chorionic gonadotrophin (Pregnyl, Organon, NZ). Each mouse was immediately placed with a CBA male stud mouse of proven fertility and checked for a seminal plug the following morning. The donors were sacrificed by cervical dislocation on the morning of either Day 1.5 post coitus for the retrieval of 2-cell embryos or Day 3.5 for late morula to blastocysts. The uterine horns were excised from the abdomen using sterile technique and placed into a plastic petri dish where they were flushed with media to expel the embryos.

Embryo BioG Insertion

An equal number of high quality embryos were selected from each donor flushing and pooled together for experimental and control groups. Experimental embryos were placed in a 50 µl micro-drop of M2 media with 2.5-5 W of BioG (50 mg/ml) for 1-1.5 hrs at 37° C. The embryos were washed three times with M2 and placed in a micro-drop of M2 in preparation for transfer. Control embryos were processed through drops of media at the same time as experimental embryos.

Embryo Transfer (ET)

To obtain a receptive endometrium in recipient mice, it is necessary to create a state of pseudopregnancy by mating with a vasectomised male mouse. The act of coitus rescues the corpus luteum of ovulated follicles from demise and sustains progesterone production necessary for implantation to occur.

Recipient CBA/C57 F1 female mice in estrus (40-120 days old), were selected from the pool of mice and placed with a vasectomised male mouse of proven sterility. The time of mating was programmed so that recipients were synchronous for 2-Cell embryos transfers or asynchronous by minus 1 day for blastocyst stage transfers. Only recipients exhibiting a clearly identified seminal plug the following morning were selected as recipients.

The recipient mice were anaesthetised with 0.8 ml of Avertin (made in-house) and an incision was made in the side of the abdomen above the hip. The fat pad above the ovary was grasped with a serrafin clamp to withdraw the oviduct and uterus outside of the body. Using a 23-28 gauge needle, a hole was made in either the bursa of the ovary to expose the infundibulum for 2-Cell stage transfers, or the uterine horn for blastocyst stage transfers. Six to ten embryos were loaded (using a mouth piece) into a fire pulled and polished capillary pipette (approx. 150-170 µm in diameter) with mineral oil and air gaps to stabilise the embryos. The pipette was inserted into the prepared needle puncture site and the embryos expelled until the release of an air-gap was visible. The exposed reproductive tract was replaced into the abdominal cavity and the body wall and skin closed with suture. The mouse was identified with ear marking and observed until conscious.

Mice were housed singularly in cages until they were either sacrificed for identification of implantation sites or until they had given birth. The implantation (imps) and live birth (pups) rates are presented in Table 13 and 14.

All recipients were kept for 3-6 months post exposure to BioG for health assessment. The offspring were maintained for breeding of one litter to assess reproductive fitness in the second generation.

TABLE 13

Implantation rate (imps) and live-birth (pups) outcome of BioG and control embryos. Embryos were zona intact 2-cell embryos. Each transfer represents a single recipient mouse.

| Transfer | Treatment | Number of embryos Transferred | Preg. Y/N | Number of pups or imps. (%) | Comment |
|---|---|---|---|---|---|
| I | BioG & Control | BioG 6x 2-Cell Control 6x 2-Cell | Y | Imps. BioG 2x (33%) Control 2x (33%) | Each group separated into separate uterine horns Sacrificed day-7 pregnancy |
| II | BioG & Control Different coloured pups | BioG 5x 2-Cell black mice control 5x 2-Cell grey mice | Y | Pups 5x total BioG 3x black (60%) Control 2x grey (40%) | Same uterine horn ET No noticeable difference in anatomy or growth between BioG and control mice ET mum died 1 day before weaning - ?stress |
| III | BioG & Control Different coloured pups | BioG 5x 2-Cell black mice Control 5x 2-Cell grey mice | Y | Pups 5x BioG 4x black (80%) Control 1x grey (20%) | Same uterine horn ET No noticeable difference in anatomy or growth between BioG and control mice |
| IV | Control | 6x 2-Cell | Y | Pups 5x (83%) | Born 19 days post ET - normal healthy pups |
| V | BioG | 10x 2-Cell | Y | Pups 8x (80%) | Born 18 days post ET Normal healthy pups |
| VI | Control | 6x 2-Cell | N | — | |
| VII | BioG | 10x 2-Cell | N | — | Died 3 months post ET - unknown cause |
| VIII | BioG | 10x 2-Cell | Y | Pups 8x (80%) | Born 18 days post ET Normal healthy pups |
| IX | BioG | 7x 2-Cell | Y | Pups 6x (85%) | Born 18 days post ET Normal healthy pups |
| X | Control | 8x 2-Cell | Y | Pups 5x (63%) | Born 18 days post ET Normal healthy pups |
| XI | Control | 10x 2-Cell | Y | Pups 6x (60%) | Born 20 days post ET Normal healthy pups (1x runt) |

TABLE 14

Implantation rate (imps %) and live-birth outcome (pups) of BioG and control embryos. Transfers were into recipient mice at the blastocyst stage zona intact. Day-3.5 embryos were transferred into day-2.5 (Expt XII-XV) or day-3.5 (Expt. XVI-XVIII) synchronised recipient mice.

| Transfer | Treatment | No. embryos Transferred | Preg. Y/N | No. imps. Or pups | Comment |
|---|---|---|---|---|---|
| XII | BioG | 6x blasts | Y | Imps 4x (66%) | Uterine ET day-2.5 recipient Sacrificed D10 of pregnancy |
| XIII | Control | 6x blasts | Y | Imps 6x (100%) | Uterine ET day-2.5 recipient Sacrificed D10 of pregnancy |
| XIV | BioG | 6x blasts | Y | Imps 4x (66%) | Uterine ET day-2.5 recipient Sacrificed D10 of pregnancy |
| XV | Control | 8x blasts | Y | Imps 5x (63%) | Uterine ET day-2.5 recipient Sacrificed D10 of pregnancy |
| XVI | Control | 6x blasts | Y | Pups 4x (66%) | Uterine ET day-3.5 Recipients |
| XVII | BioG | 6x blasts | Y | Pups 3x (50%) | Uterine ET day-3.5 Recipients Normal healthy pups |
| XVIII | BioG | 6x blasts | Y | Pups 5x (83%) | Uterine ET day-3.5 Recipients Normal healthy pups |

The first indication that BioG 2-cell embryos were capable of implantation was in a recipient mouse that had 6 BioG inserted embryos replaced into one uterine horn and 6 untreated control embryos replaced into the other horn (Transfer I). An inspection of the excised uteri on Day 7 of pregnancy revealed 4 implantation sites in each horn.

The second experimental evidence showed that not only were BioG 2-Cell embryos capable of implantation but they also gave rise to live healthy pups. In transfers II and III, five embryos derived from a pure black strain of mice (C57 donor and stud) were inserted with BioG and replaced into the same uterine horn as five control embryos derived from a pure grey strain of mouse (CBA donor and stud). The resulting colour of the 10 offspring, combined from both recipient mothers, was 3 grey (control embryos) and 7 black (BioG) babies.

Further ET experiments utilising embryos at two different stages of development, 2-cell and blastocyst, revealed similar pregnancy and live birth rates between BioG embryos and untreated control embryos for both stages of development. Overall, 8 out of 9 embryo transfers of BioG embryos resulted in a pregnancy with a live birth rate of 72.0%. The transfer of control embryos resulted in a pregnancy for 6 out of 7 ETs, with a 72.5% live birth rate.

In conclusion, the insertion of BioG in zona intact embryos from 2-cell to blastocyst stage does not appear to significantly impair the implantation and ongoing development of the embryo to live birth of healthy pups.

Example 17

The viability of zona free and zona intact murine embryos, inserted with biotinylated ganglioside (BioG) and conjugated sequentially with avidin (Av) and biotinylated IgG was confirmed by the birth of live pups post embryo transfer. Embryo retrieval and transfer of blastocysts was carried out using the methodology previously described in Example 16.

The data outlined in Table 15 showed similar live birth rates were observed for experimental and control treated embryos in both the ZI and ZF groups (experimental and control respectively: ZI 61% vs 33%, ZF 83% vs 71.5%). The primary aim of this series of experiments was not to compare implantation or live birth rates, hence the small numbers and subsequent lack of statistical analysis. The results do however confirm that ZI and ZF embryos inserted with the complete BioG/Av/BioIgG molecule give rise to healthy live pups.

Example 18

The reproductive fitness of experimental offspring and the health of the offspring proved to be similar to other inbred mice within the same animal facility. Offspring from embryo transfer experiments were paired in cages and allowed to breed. All pairs produced a litter within 75 days of birth. The mean size of the litter was 6.2 pups with normal appearance (Table 16).

TABLE 16

Number of pups delivered in 1$^{st}$ litter from experimental offspring.

| Experimental Origin and Pair | Treatment | No. of pups in 1$^{st}$ litter |
| --- | --- | --- |
| Example 4 VII | BioG | 8 |
| Example 4 VIII | BioG | 5 |
| Example 4 XI | BioG | 8 |
| Example 5 I | BioG/Av/BioIgG | 4 |
| Example 5 IV | BioG/Av/BioIgG | 7 |
| Example 5 III | Control ZI | 5 |
| Example 5 V | BioG/Av/BioIgG | 10 |
| Example 5 VI | Pronase BioG/Av/BioIgG | 6 |
| Example 5 VII | Pronase BioG/Av/BioIgG | 3 |

TABLE 15

Pregnancy outcome, number of pups and live birth rate (LB % - number of pups divided by number of embryos transfer) of BioG/Av/BioIgG blastocysts (blasts.) zona intact and zona free.

| Transfer | Treatment type | No. embryos transferred | Preg. Y/N | No. pups (LB %) | Comment |
| --- | --- | --- | --- | --- | --- |
| I | BioG/Av/BioIgG | 6x blasts zona intact | Y | Pups 5x 83% | Born 16 days post ET Normal healthy pups |
| II | Control | 6x blasts zona intact | N | — | — |
| III | Control | 6x blasts zona intact | Y | Pups 2x 33% | Born 16 days post ET Normal healthy pups |
| IV | BioG/Av/BioIgG | 6x late morula zona intact | Y | Pups 3x 50% | Born 17 days post ET Normal healthy pups |
| V | BioG/Av/BioIgG | 6x late morula zona intact | Y | Pups x3 50% | Born 17 days post ET Normal healthy pups (1x died) |
| VI | Pronase BioG/Av/BioIgG | 6x blasts zona free | Y | Pups 6x 100% | Born 16 days post ET Normal healthy pups (1x died) |
| VII | Pronase BioG/Av/BioIgG | 6x blasts zona free | Y | Pups 6x 100% | Born 16 days post ET Normal healthy pups |
| VIII | Pronase Control | 6x blasts zona free | Y | Pups 5x 83% | Born 17 days post ET Normal healthy pups |

TABLE 15-continued

Pregnancy outcome, number of pups and live birth rate (LB % - number of pups divided by number of embryos transfer) of BioG/Av/BioIgG blastocysts (blasts.) zona intact and zona free.

| Transfer | Treatment type | No. embryos transferred | Preg. Y/N | No. pups (LB %) | Comment |
|---|---|---|---|---|---|
| IX | Pronase Control | 6x blasts zona free | Y | Pups 4x 66% | Born 16 days post ET Normal healthy pups |
| X | Pronase BioG/Av/BioIgG | 6x blasts zona free | Y | Pups 3x 50% | Born 16 days post ET Normal healthy pups |

REFERENCES

Blake D A, Proctor M, Johnson N. Olive D. (2002) Cleavage stage versus blastocyst stage embryo transfer in assisted conception. *The Cochrane Library*

Bovin, N. V. "[Carbohydrate-carbohydrate interaction]." Biokhimiia. 61.6 (1996): 968-83.

Edwards, R. G., Fishel, S. B., Cohen, J. et al (1986). Factors influencing the success of in-vitro fertilisation for alleviating human infertility. *J IVF & ET,* 1: 3-23.

Ertzeid, G., and Storeng, R. (2001). The impact of ovarian stimulation on implantation and fetal development in mice. *Hum Reprod* 16: 221-225.

Feichtinger, W., Barad, D., Feinman, M., et al. (1990). The use of two-component fibrin sealant for embryo transfer. *Fertil Steril* 54: 733-734.

Feichtinger, W., Strohmer, H., Radner, K. M., et al. (1992). The use of fibrin sealant for embryo transfer: development and clinical studies. *Hum Reprod* 7: 890-893.

Garcia, J. E., Acosta, A. A., Hsiu, J. G., et al. (1984). Advanced endometrial maturation after ovulation induction with human menopausal gonadotropin/human chorionic gonadotropin for in vitro fertilisation. *Fertil Steril* 41: 31-35.

Gardner, D. K., Martinez, H. R., and Lane, M. (1999). Fetal development after transfer is increased by replacing protein with the glycosaminoglycan hyaluronan for mouse embryo culture and transfer. *Hum Reprod* 14: 2575.

Gott, A. L., Hardy, L., Winstone, R. M. L. et al (1990). Non-invasive measurements of pyruvate and glucose uptake and lactate production by single human preimplantation embryos. *Hum Reprod* 5: 104-108.

Hakomori, S. "Tumor malignancy defined by aberrant glycosylation and sphingo(glyco)lipid metabolism." Cancer Res. 56.23 (1996): 5309-18.

Hurst, T., and Lancaster, P. (2001). Assisted conception Australia and New Zealand 1999 and 2000. The University of New South Wales Annual Report 1-33

Indiveri, F., Wilson, B. S., Pellegrino, M. A. et al (1979). Detection of human histocompatibility (HLA) antigens with an indirect rosette microassay. *J Immunol Methods* 29: 101-109

Karlsson, K. A. (1987) Preparation of total non-acid glycolipids for overlay analysis of receptors for bacteria and viruses and for other studies. *Methods Enzymol* 138: 212-221.

Ladisch, S., Gillar, B. (1987). Isolation and purification of gangliosides from plasma. *Methods Enzymol* 138: 300-306

Lau, C., Vogel, R., Obe, G., et al. (1991). Embryologic and cytogenetic effects of ethanol on preimplantation mouse embryos in vitro. *Reprod Tox* 5: 405-410.

Ledeen, R. W., Yu, R. K., (1982). Gangliosides: structure, isolation and analysis. *Methods Enzymol* 83:

Mikhalchik, E. V., S. D. Shiyan, and N. V. Bovin. "Carbohydrate-carbohydrate interaction: zymosan and beta-glucan from *Saccharomyces cerevisiae* bind mannosylated glycoconjugates." Biochemistry (Mosc.) 65.4 (2000): 494-501.

Noyes, R. W., Hertig, A. T., and Rock, J. (1950). Dating the endometrial biopsy. *Fertil Steril* 1: 3-25.

Nygren, K. G., and Andersen, A. N. (2001). Assisted reproductive technology in Europe, 1997. Results generated from European registers by ESHRE. European IVF-Monitoring Programme (EIM), for the European Society of Human Reproduction and Embryology (ESHRE). *Hum Reprod* 16: 384-391.

O'Shannessy, D. L. (1990). Antibodies biotinylated via sugar moieties. *Methods Enzymol* 184:162-166

Pittaway, D. E., and Wentz, S. C. (1983). Evaluation of the exponential rise of serum estradiol concentrations in human menopausal gonadotropin induced cycles. *Fertil Steril* 40: 763-767.

Plachot, M. (1992). Viability of preimplantation embryos. *Baillieres clin Obst Gynaecol.* 6: 327-338

Purdum, H E. 1999. Compositions methods and devices for embryo implantation for in vitro fertiliszation. Delphion.com. U.S. Pat. No. 6,196,965, US.

Rodrigues, F. A., Van Rensburg, J. H. J., De Vries, J., et al. (1988). The effect of fibrin sealant on mouse embryos. *Journal of in Vitro Fertilization and Embryo Transfer* 5: 158-160.

Ronnberg, L., Isotalo, H., Kauppila, A., et al. (1985). Clomiphene-induced changes in endometrial receptor kinetics on the day of ovum collection after ovarian stimulation: A study of cytosol and nuclear estrogen adn progestin receptors and 17beta-hydroxysteroid dehydrogenase. *Ann N Y Acad Sci* 442: 408-415.

Simon C, Landeras J, Zuzuarregui J L, Martin J C, Remohi J, Pellicer A. (1999) Early pregnancy losses in vitro fertilization and oocyte donation. *Fertil Steril* 72:1061-1065

Sjoblom, C., Hyllner, S. J., Wikland, M., et al. (2000). Superovulation increases the incidence of cell death in murine blastocysts. *ASRM Conference Abstract Book*: S17.

Sneath, J. S., and Sneath, P. H. A. (1959). Adsorption of blood-group substances from serum on to red cells. *British Medical Journal* 15:154-157.

van Kooij, R. J., Looman, C. W., Habbema, J. D. et al (1996). Age-dependent decrease in embryo implantation rate after in vitro fertilization. *Fertil Steril* 66: 769-775.

Wang, X. et al. "Carbohydrate-carbohydrate binding of ganglioside to integrin alpha(5) modulates alpha(5)beta(1)-function." J Biol Chem 276.11 (2001): 8436-44.

Yaron, Y., Botchan, A., Amit, A. et al (1994). Endometrial receptivity in the light of modern assisted reproductive technologies. *Fertil Steril,* 62: 225-323.

Zhang, F., Schmidt, W. G., Hou, Y., et al. (1992). Spontaneous incorporation of the glycosyl-phosphatidylinositol-linked protein Thy-1 into cell membranes. *Proc Natl Acad Sci USA* 89: 5231-5235.

Zom, T. M., Pinhal, M. A., Nader, H. B., et al. (1995). Biosynthesis of glycosaminoglycans in the endometrium during the initial stages of pregnancy of the mouse. *Cell Mol Biol (Noisy-le-grand)* 41: 97-106.

What is claimed is:

1. A method of enhancing the implantation of an embryo into the endometrium of an animal including the steps:
   a. modifying the embryo to incorporate a glycolipid-attachment molecule construct; and
   b. transferring the modified embryo to the uterus of the animal;
   where a glycolipid is exogenously modified to incorporate a binding part adapted to enable the modified glycolipid to bind the attachment molecule.

2. A method as claimed in claim 1 where the modified glycolipid is bound to an attachment molecule modified to incorporate a binding part adapted to enable the modified attachment molecule to bind to the modified glycolipid either indirectly through a bridging molecule or directly.

3. A method as claimed in claim 2 where the modification to the glycolipid is to the carbohydrate portion of the glycolipid.

4. A method as claimed in claim 2 wherein the attachment molecule is selected from the group consisting of: natural or synthetic carbohydrates or oligosaccharides; glycolipids; glycoconjugates; proteins or peptides; acyl groups; and polymers.

5. A method as claimed in claim 4 where the attachment molecule is selected from the group consisting of: poly L-lysine; antibodies;
   lectins; polyvinyl pyrrolidine; and functionally equivalent derivatives thereof.

6. A method as claimed in claim 5 wherein the attachment molecule is an immunoglobulin.

7. A method as claimed in claim 6 wherein the attachment molecule is immunoglobulin G (IgG).

8. A method as claimed in claim 2 where the attachment molecule is adapted to interact with the epithelial cells of the endometrium, mucus, mucin, or other endogenous or exogenously provided component of mucus.

9. A method as claimed in claim 8 where the attachment molecule is an endometrial attachment molecule.

10. A method as claimed in claim 2 where the glycolipid is selected from the group consisting of phosphoglycerides and sphingolipids.

11. A method as claimed in claim 2 where the attachment molecule and the glycolipid are bound together by simple non-covalent binding interactions including ionic, van de Waals, water exclusion, electrostatic, hydrogen bonding and chelation binding.

12. A method as claimed in claim 2 where the attachment molecule and the glycolipid are bound together by covalent bonding.

13. A method as claimed in claim 2 where the attachment molecule and the glycolipid are bound together by avidin-biotin binding.

14. A method as claimed in claim 13 where the binding part of the glycolipid comprises biotin and the binding part of the attachment molecule comprises avidin.

15. A method as claimed in claim 13 where the binding part of the glycolipid comprises avidin and the binding part of the attachment molecule comprises biotin.

16. A method as claimed in claim 13 where the attachment molecules and the glycolipid are bound together through a bridging molecule.

17. A method as claimed in claim 16 where the bridging molecule comprises avidin and the binding part of both the attachment molecule and the glycolipid comprises biotin.

18. A method as claimed in claim 16 wherein the bridging molecule comprises biotin and the binding part of both the attachment molecule and the glycolipid comprises avidin.

19. A method as claimed in claim 2 where the attachment molecule and the glycolipid are bound together by a chelation interation between at least one chelator and a chelated metal ion.

20. A method as claimed in claim 19 wherein the binding part of both the attachment molecule and the glycolipid comprises a chelator.

21. A method as claimed in claim 19 wherein the chelator is a poly-histidine recombinant protein.

22. A method as claimed in claim 19 where the chelator is attached covalently to the glycolipid.

23. A method as claimed in claim 19 where the chelator is attached non-covalently to the glycolipid.

24. A method as claimed in claim 23 wherein the chelator is attached to the glycolipid via biotin or avidin.

25. A method as claimed in claim 23 where the chelated metal ion is $Co^{2+}$, $Ni^{2+}$ or $Cu^{2+}$.

26. A method as claimed in claim 2 where the glycolipid modified to incorporate a binding part is a biotinylated glycolipid.

27. A method as claimed in claim 2 where the glycolipid of the ganglioside class that contains sialic acid groups, or a glycolipid of the neutral class that contains galactose.

28. A method as claimed in claim 2 where the attachment molecule is a molecule that has a binding affinity for molecules on cell membranes including the mucus coat of cell membranes.

29. A method as claimed in claim 28 wherein the molecules on cell membranes are receptor sites and/or blood group related antigens.

30. A method as claimed in claim 29 where the cell membranes are endometrial.

31. A method as claimed in claim 1 where the animal is a human or domesticated animal.

32. A method as ,claimed in claim 1 where the modified embryo is prepared from a species, hybrid or variety of animal different from the species, hybrid or variety of animal of the uterus.

* * * * *